(12) United States Patent
Manley et al.

(10) Patent No.: US 6,458,814 B1
(45) Date of Patent: Oct. 1, 2002

(54) VITRONECTIN RECEPTOR ANTAGONISTS

(75) Inventors: Peter J. Manley, Harleysville; William H. Miller, Collegeville, both of PA (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 09/762,406

(22) PCT Filed: Aug. 3, 1999

(86) PCT No.: PCT/US99/17665

§ 371 (c)(1),
(2), (4) Date: Feb. 7, 2001

(87) PCT Pub. No.: WO00/07544

PCT Pub. Date: Feb. 17, 2000

Related U.S. Application Data

(60) Provisional application No. 60/095,703, filed on Aug. 7, 1998.

(51) Int. Cl.[7] .................. C07D 413/12; A61K 31/4439; A61P 19/10
(52) U.S. Cl. ..................................... 514/340; 546/269.4
(58) Field of Search .................. 546/269.4; 514/340

(56) References Cited

U.S. PATENT DOCUMENTS 6,103,711 A * 8/2000 Bemis et al. ............. 514/183

FOREIGN PATENT DOCUMENTS

EP 0 519 738 A1 6/1992

* cited by examiner

*Primary Examiner*—Joseph K. McKane
*Assistant Examiner*—Kamal Saeed
(74) *Attorney, Agent, or Firm*—Laura K. Madden; Mary E. McCarthy; Charles M. Kinzig

(57) ABSTRACT

Compounds of the formula (I) are disclosed which are vitronectin receptor antagonists and are useful in the treatment of osteoporosis:

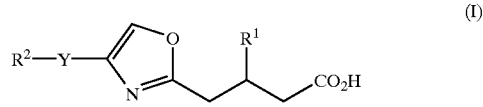

or a pharmaceutically acceptable salt thereof.

27 Claims, No Drawings

VITRONECTIN RECEPTOR ANTAGONISTS

This application is a 371 of PCT/US99/17665 filed Aug. 3, 1999, which claims benefit from the following U.S. Provisional Application No. 60/095,703 filed Aug. 7, 1998.

FIELD OF THE INVENTION

This invention relates to pharmaceutically active compounds which inhibit the vitronectin receptor and are useful for the treatment of inflammation, cancer and cardiovascular disorders, such as atherosclerosis and restenosis, and diseases wherein bone resorption is a factor, such as osteoporosis.

BACKGROUND OF THE INVENTION

Integrins are a superfamily of cell adhesion receptors, which are transmembrane glycoproteins expressed on a variety of cells. These cell surface adhesion receptors include gpII/IIIa (the fibrinogen receptor) and $\alpha_v\beta_3$ (the vitronectin receptor). The fibrinogen receptor gpIIb/IIIa is expressed on the platelet surface, and mediates platelet aggregation and the formation of a hemostatic clot at the site of a bleeding wound. Philips, et al., *Blood.*, 1988, 71, 831. The vitronectin receptor $\alpha_v\beta_3$ is expressed on a number of cells, including endothelial, smooth muscle, osteoclast, and tumor cells, and, thus, it has a variety of functions. The $\alpha_v\beta_3$ receptor expressed on the membrane of osteoclast cells mediates the adhesion of osteoclasts to the bone matrix, a key step in the bone resorption process. Ross, et al., *J. Biol. Chem*, 1987, 262, 7703. A disease characterized by excessive bone resorption is osteoporosis. The $\alpha_v\beta_3$ receptor expressed on human aortic smooth muscle cells mediates their migration into neointima, a process which can lead to restenosis after percutaneous coronary angioplasty. Brown, et al., *Cardiovascular Res.*, 1994, 28, 1815. Additionally, Brooks, et al., *Cell,* 1994, 79, 1157 has shown that an $\alpha_v\beta_3$ antagonist is able to promote tumor regression by inducing apoptosis of angiogenic blood vessels. Thus, agents that block the vitronectin receptor would be useful in treating diseases, such as osteoporosis, restenosis and cancer.

The vitronectin receptor is now known to refer to three different integrins, designated $\alpha_v\beta_1$, $\alpha_v\beta_3$ and $\alpha_v\beta_5$. Horton, et al., *Int. J. Exp. Pathol.*, 1990, 71,741. $\alpha_v\beta_1$ binds fibronectin and vitronectin. $\alpha_v\beta_3$ binds a large variety of ligands, including fibrin, fibrinogen, laminin, thrombospondin, vitronectin, von Willebrand's factor, osteopontin and bone sialoprotein I. $\alpha_v\beta_5$ binds vitronectin. The vitronectin receptor $\alpha_v\beta_5$ has been shown to be involved in cell adhesion of a variety of cell types, including microvascular endothelial cells, (Davis, et al., *J. Cell. Biol.*, 1993, 51, 206), and its role in angiogenesis has been confirmed. Brooks, et al., *Science,* 1994, 264, 569. This integrin is expressed on blood vessels in human wound granulation tissue, but not in normal skin.

The vitronectin receptor is known to bind to bone matrix proteins which contain the tri-peptide Arg-Gly-Asp (or RGD) motif. Thus, Horton, et al., *Exp. Cell Res.* 1991, 195, 368, disclose that RGD-containing peptides and an anti-vitronectin receptor antibody (23C6) inhibit dentine resorption and cell spreading by osteoclasts. In addition, Sato, et al., *J. Cell Biol.* 1990, 111, 1713 discloses that echistatin, a snake venom peptide which contains the RGD sequence, is a potent inhibitor of bone resorption in tissue culture, and inhibits attachment of osteoclasts to bone.

It has now been discovered that certain compounds are potent inhibitors of the $\alpha_v\beta_3$ and $\alpha_v\beta_5$ receptors. In particular, it has been discovered that such compounds are more potent inhibitors of the vitronectin receptor than the fibrinogen receptor.

SUMMARY OF THE INVENTION

This invention comprises compounds of the formula (I) as described hereinafter, which have pharmacological activity for the inhibition of the vitronection receptor and are useful in the treatment of inflammation, cancer and cardiovascular disorders, such as atherosclerosis and restenosis, and diseases wherein bone resorption is a factor, such as osteoporosis.

This invention is also a pharmaceutical composition comprising a compound according to formula (I) and a pharmaceutically carrier.

This invention is also a method of treating diseases which are mediated by the vitronectin receptor. In a particular aspect, the compounds of this invention are useful for treating atherosclerosis, restenosis, inflammation, cancer and diseases wherein bone resorption is a factor, such as osteoporosis.

DETAILED DESCRIPTION

This invention comprises novel compounds which are more potent inhibitors of the vitronectin receptor than the fibrinogen receptor. This invention comprises compounds of formula (I):

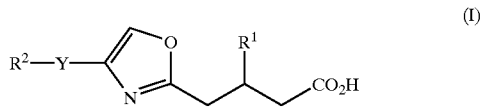

wherein:

Y is CR'R' or NR'C(O);

$R^1$ is —$C_{0-6}$alkyl-Het-, —$C_{0-6}$alkyl-Ar, H, —$C_{1-6}$alkyl, —CN or —S(O)$_k$R$^8$;

$R^2$ is

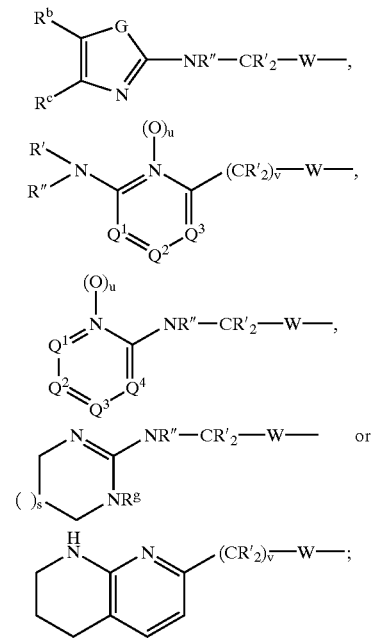

W is —(CHR$^g$)$_a$—U—(CHR$^g$)$_b$—;

U is absent or CO, CR$^g$$_2$, C(=CR$^g$$_2$), S(O)$_k$, O, NR$^g$, CR$^g$OR$^g$, CR$^g$(OR$^k$)CR$^g$$_2$, CR$^g$$_2$CR$^g$(OR$^k$), C(O)CR$^g$$_2$, CR$^g$$_2$C(O), CONR$^i$, NR$^i$CO, OC(O), C(O)O, C(S)O, OC(S), C(S)NR$^g$, NR$^g$C(S), S(O)$_2$NR$^g$, NR$^g$S(O)$_2$ N=N, NR$^g$NR$^g$, NR$^g$CR$^g$$_2$, CR$^g$$_2$NR$^g$, CR$^g$$_2$O, OCR$^g$$_2$, C≡C, CR$^g$=CR$^g$, Ar or Het;

G is NR$^e$, S or O;

R$^g$ is H, C$_{1-6}$alkyl, Het—C$_{0-6}$alkyl, C$_{3-7}$cycloalkyl-C$_{0-6}$alkyl or Ar—C$_{0-6}$alkyl;

R$^k$ is R$^g$, —C(O)R$^g$, or —C(O)OR$^f$;

R$^i$ is is H, C$_{1-6}$alkyl, Het—C$_{0-6}$alkyl, C$_{3-7}$cycloalkyl-C$_{0-6}$alkyl, Ar—C$_{0-6}$alkyl, or C$_{1-6}$alkyl substituted by one to three groups chosen from halogen, CN, NR$^g$$_2$, OR$^g$, SR$^g$, CO$_2$R$^g$, and CON(R$^g$)$_2$;

R$^f$ is H, C$_{1-6}$alkyl or Ar—C$_{0-6}$alkyl;

R$^e$ is H, C$_{1-6}$alkyl, Ar—C$_{0-6}$alkyl, Het—C$_{0-6}$alkyl, C$_{3-7}$cycloalkyl-C$_{0-6}$, or (CH$_2$)$_k$CO$_2$R$^g$;

R$^b$ and R$^c$ are independently selected from H, C$_{1-6}$alkyl, Ar—C$_{0-6}$alkyl, Het—C$_{0-6}$alkyl, or C$_{3-6}$cycloalkyl-C$_{0-6}$alkyl, halogen, CF$_3$, OR$^f$, S(O)$_k$R$^f$, COR$^f$, NO$_2$, N(R$^f$)$_2$, CO(NR$^f$)$_2$, CH$_2$N(R$^f$)$_2$, or R$^b$ and R$^c$ are joined together to form a five or six membered aromatic or non-aromatic carbocyclic or heterocyclic ring, optionally substituted by up to three substituents chosen from halogen, CF$_3$, C$_{1-4}$alkyl, OR$^f$, S(O)$_k$R$^f$, COR$^f$, CO$_2$R$_f$OH, NO$_2$, N(R$^f$)$_2$, CO(NR$^f$)$_2$, and CH$_2$N(R$^f$)$_2$; or methylenedioxy;

Q$^1$, Q$^2$, Q$^3$ and Q$^4$ are independently N or C—R$^v$, provided that no more than one of Q$^1$, Q$^2$, Q$^3$ad Q$^4$is N;

R' is H, C$_{1-6}$alkyl, Ar—C$_{0-6}$alkyl or C$_{3-6}$cycloalkyl-C$_{0-6}$alkyl;

R" is R', —C(O)R' or —C(O)OR';

R$^v$ is H, halo, —OR$^g$, —SR$^g$, —CN, —NR$^g$R$^k$, —NO$_2$, —CF$_3$, CF$_3$S(O)$_r$—, —CO$_2$R$^g$, —COR$^g$ or —CONR$^g$$_2$, or C$_{1-6}$alkyl optionally substituted by halo, —OR$^g$, —SR$^g$, —CN, —NR$^g$R", —NO$_2$, —CF$_3$, R'S(O)$_r$—, —CO$_2$R$^g$, —COR$^g$ or —CONR$^g$$_2$;

a is 0, 1 or 2;

b is 0, 1 or 2;

k is 0, 1 or 2;

r is 0, 1 or 2;

s is 0, 1 or 2;

u is 0 or 1; and v is 0 or 1;

or a pharmaceutically acceptable salt thereof.

Also included in this invention are pharmaceutically acceptable addition salts and complexes of the compounds of this invention. In cases wherein the compounds of this invention may have one or more chiral centers, unless specified, this invention includes each unique nonracemic compound which may be synthesized and resolved by conventional techniques. In cases in which compounds have unsaturated carbon-carbon double bonds, both the cis (Z) and trans (E) isomers are within the scope of this invention. In case, wherein compounds may exist in tautomeric forms, such as keto-enol tautomers, such as

and

and each tautomeric form is contemplated as being included within this invention whether existing in equilibrium or locked in one form by appropriate substitution with R'.

The compounds of formula (I) inhibit the binding of vitronectin and other RGD-containing peptides to the vitronectin receptor. Inhibition of the vitronectin receptor on osteoclasts inhibits osteoclastic bone resorption and is useful in the treatment of diseases wherein bone resorption is associated with pathology, such as osteoporosis and osteoarthritis.

In another aspect, this invention is a method for stimulating bone formation which comprises administering a compound which causes an increase in osteocalcin release. Increased bone productiorinis a clear benefit in disease states wherein there is a deficiency of mineralized bone mass or remodeling of bone is desired, such as fracture healing and the prevention of bone fractures. Diseases and metabolic disorders which result in loss of bone structure would also benefit from such treatment. For instance, hyperparathyroidism, Paget's disease, hypercalcemia of malignancy, osteolytic lesions produced by bone metastasis, bone loss due to immobilization or sex hormone deficiency, Behçet's disease, osteomalacia, hyperostosis and osteopetrosis. could benefit from administering a compound of this invention.

Additionally, since the compounds of the instant invention inhibit vitronectin receptors on a number of different types of cells, said compounds would be useful in the treatment of inflammatory disorders, such as rheumatoid arthritis and psoriasis, and cardiovascular diseases, such as atherosclerosis and restenosis. The compounds of Formula (I) of the present invention may be useful for the treatment or prevention of other diseases including, but not limited to, thromboembolic disorders, asthma, allergies, adult respiratory distress syndrome, graft versus host disease, organ transplant rejection, septic shock, eczema, contact dermatitis, inflammatory bowel disease, and other autoimmune diseases. The compounds of the present invention may also be useful for wound healing.

The compounds of the present invention are also useful for the treatment, including prevention, of angiogenic disorders. The term angiogenic disorders as used herein includes conditions involving abnormal neovascularization. Where the growth of new blood vessels is the cause of, or contributes to, the pathology associated with a disease, inhibition of angiogenisis will reduce the deleterious effects of the disease. An example of such a disease target is diabetic retinopathy. Where the growth of new blood vessels is required to support growth of a deleterious tissue, inhibition of angiogenisis will reduce the blood supply to the tissue and thereby contribute to reduction in tissue mass based on blood supply requirements. Examples include growth of tumors where neovascularization is a continual requirement in order that the tumor grow and the establishment of solid tumor metastases. Thus, the compounds of the present invention inhibit tumor tissue angiogenesis, thereby preventing tumor metastasis and tumor growth.

Thus, according to the methods of the present invention, the inhibition of angiogenesis using the compounds of the present invention can ameliorate the symptoms of the disease, and, in some cases, can cure the disease.

Another therapeutic target for the compounds of the instant invention are eye diseases chacterized by neovascularization. Such eye diseases include corneal neovascular disorders, such as corneal transplantation, herpetic keratitis, luetic keratitis, pterygium and neovascular pannus associated with contact lens use. Additional eye diseases also include age-related macular degeneration, presumed ocular histoplasmosis, retinopathy of prematurity and neovascular glaucoma.

This invention further provides a method of inhibiting tumor growth which comprises administering stepwise or in physical combination a compound of formula (I) and an antineoplastic agent, such as topotecan and cisplatin.

With respect to formula (I):

Suitably $R^2$ is

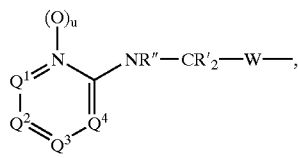

wherein, $Q^1$, $Q^2$, and $Q^3$ are each $CR^y$, $Q^4$ is $CR^y$ or N and u is 0, and preferably, each R' is H, R" is H or $C_{1-6}$alkyl, W is —$(CH_2)_{1-4}$—, $Q^4$ is $CR^y$ and $R^y$ is H.

Alternately $R^2$ is

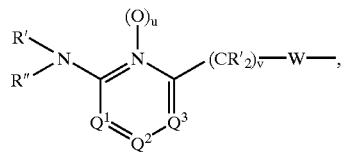

wherein $Q^1$, $Q^2$, and $Q^3$ are each CH and u is 0, and preferably, each R' is H, R" is H or $C_{1-6}$alkyl, W is —$(CH_2)_{1-4}$— and v is 0.

Alternately $R^2$ is

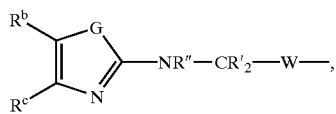

wherein G is NH and $R^b$ and $R^c$ are each H, and preferably, W is —$(CH_2)_{1-4}$—.

Alternately $R^2$ is

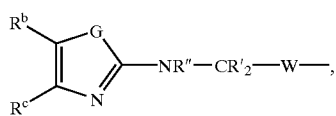

wherein G is NH and $R^b$ and $R^c$ are joined together to form a five or six membered aromatic or non-aromatic carbocyclic or heterocyclic ring, optionally substituted by up to three substituents chosen from halogen, $CF_3$, $C_{1-4}$alkyl, $OR^f$, $S(O)_kR^f$, $COR^f$, $CO_2R^f$, OH, $NO_2$, $N(R^f)_2$, $CO(NR_f)_2$, and $CH_2N(R^f)_2$; or methylenedioxy. Preferably, $R^b$ and $R^c$ are joined together to form a six membered aromatic carbocyclic or heterocyclic ring and W is —$(CH_2)_{1-4}$—.

Alternately $R^2$ is

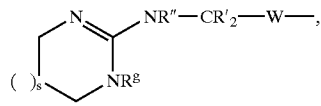

wherein each R' is H, R" is H or $C_{1-6}$alkyl, $R^g$ is H or $C_{1-6}$alkyl and s is 0, 1 or 2 and, preferably, W is —$(CH_2)_{1-4}$—.

With respect to formula (I), suitably $R^1$ is is phenyl, benzyl, pyridyl, imidazolyl, oxazolyl or thiazolyl. Preferably, $R^1$ is phenyl. Suitably, Y is NHC(O).

Representative of the novel compounds of this invention are the following:

(±)-3-phenyl-4-[4-[[[3-(pyridin-2-yl)amino-1-propyl]amino]carbonyl]-1,3-oxazol-2-yl]butanoic acid;

(±)-3-phenyl-4-[4-[[[2-(pyridin-2-yl)amino-1-ethyl]amino]carbonyl]-1,3-oxazol -2-yl]butanoic acid;

(±)-3-phenyl-4-[4-[[[4-(pyridin-2-yl)amino-1-butyl]amino]carbonyl]-1,3-oxazol -2-yl]butanoic acid; and (±)-3-phenyl-4-[4-[5-(pyridin-2-yl)amino-1-pentyl]-1,3-oxazol-2-yl]butanoic acid;

or a pharmaceutically acceptable salt thereof.

In cases wherein the compounds of this invention may have one or more chiral centers, unless specified, this invention includes each unique nonracemic compound which may be synthesized and resolved by conventional techniques. According to the present invention, the (S) configuration of the formula (I) compounds is preferred.

In cases in which compounds have unsaturated carbon-carbon double bonds, both the cis (Z) and trans (E) isomers are within the scope of this invention. The meaning of any substituent at any one occurrence is independent of its meaning, or any other substituent's meaning, at any other occurrence.

Also included in this invention are prodrugs of the compounds of this invention. Prodrugs are considered to be any covalently bonded carriers which release the active parent drug according to formula (I) in vivo. Thus, in another aspect of this invention are novel prodrugs, which are also intermediates in the preparation of formula (I) compounds, of formula (II):

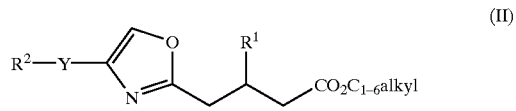

(II)

wherein:

Y is CR'R' or NR'C(O);

$R^1$ is —$C_{0-6}$alkyl-Het—, —$C_{0-6}$alkyl-Ar, H, —$C_{1-6}$alkyl, —CN or —$S(O)_kR^g$;

$R^2$ is

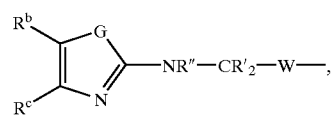

-continued

[chemical structure]

[chemical structure]

[chemical structure]

[chemical structure]

W is —(CHR$^g$)$_a$—U—(CHR$^g$)$_b$—;

U is absent or CO, CR$^g{}_2$, C(=CR$^g{}_2$), S(Q)$_k$, O, NR$^g$, CR$^g$OR$^g$, CR$^g$(OR$^k$)CR$^g{}_2$, CR$^g{}_2$CR$^g$(OR$^k$), C(O)CR$^g{}_2$, CR$^g{}_2$C(O), CONR$^i$, NR$^i$CO, OC(O), C(O)O, C(S)O, OC(S), C(S)NR$^g$, NR$^g$C(S), S(O)$_2$NR$^g$, NR$^g$S(O)$_2$ N=N, N$^g$NR$^g$, NR$^g$CR$^g{}_2$, CR$^g{}_2$NR$^g$, CR$^g{}_2$O, OCR$^g{}_2$, C≡C, CR$^g$=CR$^g$, Ar or Het;

G is NR$^e$, S or O;

R$^g$ is H, C$_{1-6}$alkyl, Het—C$_{0-6}$alkyl, C$_{3-7}$cycloalky-C$_{0-6}$alkyl or Ar—C$_{0-6}$alkyl;

R$^k$ is R$^g$, —C(O)R$^g$, or —C(O)OR$^f$;

R$^i$ is is H, C$_{1-6}$alkyl, Het—C$_{0-6}$alkyl, C$_{3-7}$cycloalkyl-C$_{0-6}$alkyl, Ar—C$_{0-6}$alkyl, or C$_{1-6}$alkyl substituted by one to three groups chosen from halogen, CN, NR$^g{}_2$, OR$^g$, SR$^g$, CO$_2$R$^g$, and CON(R$^g$)$_2$;

R$^f$ is H, C$_{1-6}$alkyl or Ar—C$_{0-6}$alkyl;

R$^e$ is H, C$_{1-6}$alkyl, Ar—C$_{0-6}$alkyl, Het—C$_{0-6}$alkyl, C$_{3-7}$cycloalkyl-C$_{0-6}$alkyl, or (CH$_2$)$_k$CO$_2$R$^f$;

R$^b$ and R$^c$ are independently selected from H, C$_{1-6}$alkyl, Ar—C$_{0-6}$alkyl Het—C$_{0-6}$alkyl, or C$_{3-6}$cycloalkyl-C$_{0-6}$alkyl, halogen, CF$_3$, OR$^f$, S(O)$_k$R$^f$, COR$^f$, NO$_2$, N(R$^f$)$_2$, CO(NR$^f$)$_2$, CH$_2$N(R$^f$)$_2$, or R$^b$ and R$^c$ are joined together to form a five or six membered aromatic or non-aromatic carbocyclic or heterocyclic ring, optionally substituted by up to three substituents chosen from halogen, CF$_3$, C$_{1-4}$alkyl, OR$^f$, S(O)$_k$R$^f$, COR$^f$, CO$_2$R$^f$, OH, NO$_2$, N(R$^f$)$_2$, CO(NR$^f$)$_2$, and CH$_2$N(R$^f$)$_2$; or methylenedioxy;

Q$^1$, Q$^2$, Q$^3$ and Q$^4$ are independently N or C—R$^y$, provided that no more than one of Q$^1$, Q$^2$, Q$^3$ and Q$^4$ is N;

R' is H, C$_{1-6}$alkyl, Ar—C$_{0-6}$alkyl or C$_{3-6}$cycloalkyl-C$_{0-6}$alkyl;

R" is R', —C(O)R' or —C(O)OR';

R$^y$ is H, halo, —OR$^g$, —SR$^g$, —CN, —NR$^g$R$^k$, —NO$_2$, —CF$_3$, CF$_3$S(O)$_r$—, —CO$_2$R$^g$, —COR$^g$ or —CONR$^g{}_2$, or C$_{1-6}$alkyl optionally substituted by halo, —OR$^g$, —SR$^g$, —CN, —NR$^g$R", —NO$_2$, —CF$_3$, R'S (O)$_r$—, —CO$_2$R$^g$, —COR$^g$ or —CONR$^g{}_2$;

a is 0, 1 or 2;

b is 0, 1 or 2;

k is 0, 1 or 2;

r is 0, 1 or 2;

s is 0, 1 or 2;

u is 0 or 1; and v is 0 or 1;

or a pharmaceutically acceptable salt thereof.

Abbreviations and symbols commonly used in the peptide and chemical arts are used herein to describe the compounds of this invention. In general, the amino acid abbreviations follow the IUPAC-IUB Joint Commission on Biochemical Nomenclature as described in *Eur. J. Biochem,* 158, 9 (1984).

C$_{1-4}$alkyl as applied herein means an optionally substituted alkyl group of 1 to 4 carbon atoms, and includes methyl, ethyl, n-propyl, isopropyl, n-butyl, isobutyl and t-butyl. C$_{1-6}$alkyl additionally includes pentyl, n-pentyl, isopentyl, neopentyl and hexyl and the simple aliphatic isomers thereof. C$_{0-4}$alkyl and C$_{0-6}$alkyl additionally indicates that no alkyl group need be present (e.g., that a covalent bond is present).

Any C$_{1-4}$alkyl or C$_{1-6}$ alkyl, C$_{2-6}$ alkenyl, C$_{2-6}$ alkynyl or C$_{1-6}$ oxoalkyl may be optionally substituted with the group R$^x$, which may be on any carbon atom that results in a stable structure and is available by conventional synthetic techniques. Suitable groups for R$^x$ are C$_{1-4}$alkyl, OR', SR', C$_{1-4}$alkylsulfonyl, C$_{1-4}$alkylsulfoxyl, —CN, N(R')$_2$, CH$_2$N (R')$_2$, —NO$_2$, —CF$_3$, —CO$_2$R'—CON(R')$_2$, —COR', —NR'C(O)R', F, Cl, Br, I, or CF$_3$S(O)$_r$—, wherein r is 0, 1 or 2.

Halogen or halo means F, Cl, Br, and L.

Ar, or aryl, as applied herein, means phenyl or naphthyl, or phenyl or naphthyl substituted by one to three substituents, such as those defined above for alkyl, especially. C$_{1-4}$alkyl, C$_{1-4}$alkoxy, C$_{1-4}$alkthio, CF$_3$, NH$_2$, OH, F, Cl, Br or I.

Het, or heterocycle, indicates an optionally substituted five or six membered monocyclic ring, or a nine or ten-membered bicyclic ring containing one to three heteroatoms chosen from the group of nitrogen, oxygen and sulfur, which are stable and available by conventional chemical synthesis. Illustrative heterocycles are benzofuryl, benzimidazole, benzopyran, benzothiophene, furan, imidazole, indoline, morpholine, piperidine, piperazine, pyrrole, pyrrolidine, tetrahydropyridine, pyridine, thiazole, oxazole, thiophene, quinoline, isoquinoline, and tetra- and perhydro- quinoline and isoquinoline. Any accessible combination of up to three substituents on the Het ring, such as those defined above for alkyl that are available by chemical synthesis and are stable are within the scope of this invention.

C$_{3-7}$cycloalkyl refers to an optionally substituted carbocyclic system of three to seven carbon atoms, which may contain up to two unsaturated carbon-carbon bonds. Typical of C$_{3-7}$cycloalkyl are cyclopropyl, cyclobutyl, cyclopentyl, cyclopentenyl, cyclohexyl, cyclohexenyl and cycloheptyl. Any combination of up to three substituents, such as those defined above for alkyl, on the cycloalkyl ring that is available by conventional chemical synthesis and is stable, is within the scope of this invention.

When R$^b$ and R$^c$ are joined together to form a five- or six-membered aromatic or non-aromatic carbocyclic or heterocyclic ring fused to the ring to which R$^b$ and R$^c$ are attached, the ring formed will generally be a five- or six-membered heterocycle selected from those listed above for Het, or will be a phenyl, cyclohexyl or cyclopentyl ring. Preferably R$^b$ and R$^c$ will be —D1=D2—D3=D4 wherein D1–D4 are independently CH, N or C—R$_x$ with the proviso that no more than two of D1–D4 are N. Most preferably, when R$^b$ and R$^c$ are joined together they form the group —CH=CH—CH=CH—.

Certain radical groups are abbreviated herein. t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the benzyloxycarbonyl radical, Bn refers to the benzyl radical, Me refers to methyl, Et refers to ethyl, Ac refers to acetyl, Alk refers to $C_{1-4}$alkyl, Nph refers to 1- or 2-naphthyl and cHex refers to cyclohexyl. Tet refers to 5-tetrazolyl.

Certain reagents are abbreviated herein. DCC refers to dicyclohexylcarbodiimide, DMAP refers to dimethylaminopyridine, DIEA refers to diisopropylethyl amine, EDC refers to 1-(3-dimethylaminopropyl)-3-ethylcarbodiimide, hydrochloride. HOBt refers to 1-hydroxybenzotriazole, THF refers to tetrahydrofuran, DIEA refers to diisopropylethylamine, DEAD refers to diethyl azodicarboxylate, $PPh_3$ refers to triphenylphosphine, DIAD refers to diisopropyl azodicarboxylate, DME refers to dimethoxyethane, DMF refers to dimethylformamide, NBS refers to N-bromosuccinimide, Pd/C refers to a palladium on carbon catalyst, PPA refers to polyphosphoric acid, DPPA refers to diphenylphosphoryl azide, BOP refers to benzotriazol-1-yloxy-tris(dimethyl-amino)phosphonium hexafluorophosphate, HF refers to hydrofluoric acid, TEA refers to triethylamine, TFA refers to trifluoroacetic acid, PCC refers to pyridinium chlorochromate.

The compounds of formula (I) are generally prepared by reacting a compound of formula (III) with a compound of formula (IV):

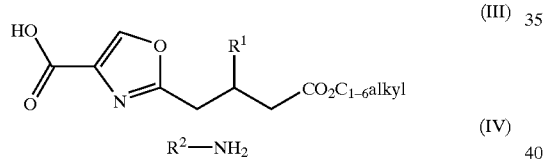

(III)

(IV)

wherein $R^1$ and $R^2$ are as defined in formula (I), with any reactive functional groups protected;

and thereafter removing any protecting groups, and optionally forming a pharmaceutically acceptable salt.

Compounds of the formula (I) are prepared by the general methods described in Schemes I–II.

Scheme I

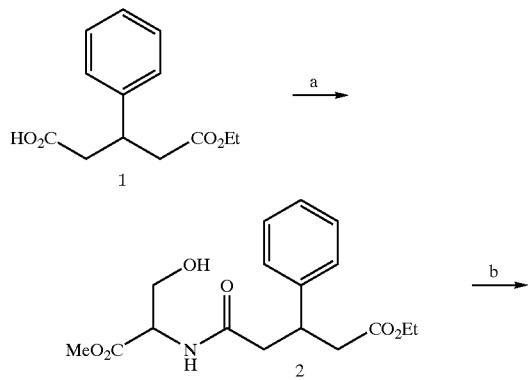

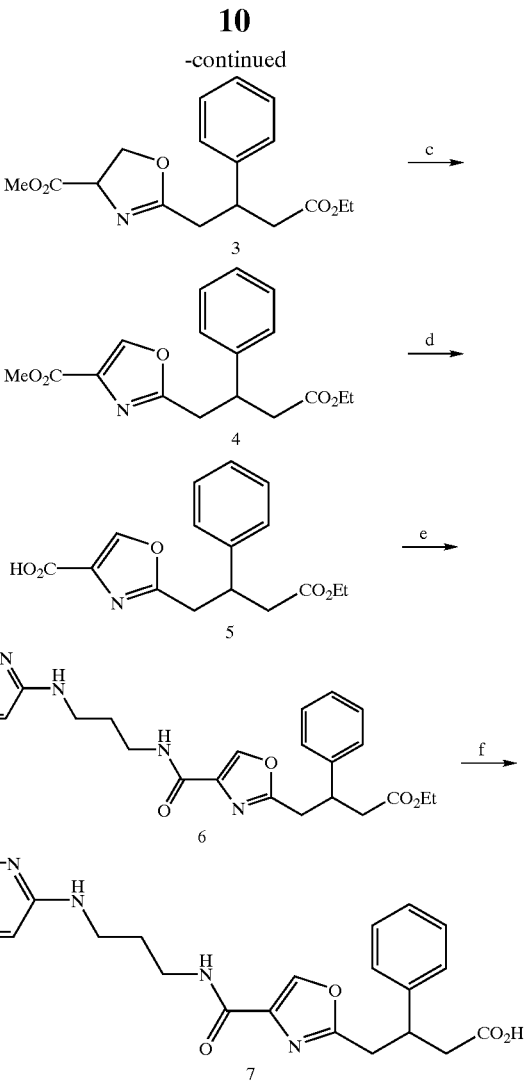

(a) serine methyl ester, EDC, $HOBt·H_2O$, $Et_3N$, DMF; (b) Burgess reagent, ThF; (c) $CuBr_2$, DBU, hexamethylenetetramine, $CH_2Cl_2$; (d) LiI, pyridine; (e) CDI, $CH_2Cl_2$, then 2-[(3-amino-1-propyl)amino]pyridine dihydrochloride, $Et_3N$; (f) LiOH, THF, $H_2O$, then acidification.

The mono-ethyl ester of 3-phenylglutaric acid (I-1; *J. Org. Chem.* 1959, 24, 1290) is converted to an activated form of the acid using, for example, EDC and HOBt, or $SOCl_2$, and the activated form is subsequently reacted with an appropriate 2-hydroxyethylamine, for instance serine methyl ester, in a suitable solvent such as DMF, $CH_2Cl_2$, or $CH_3CN$, to afford the hydroxyethylamide I-2. Depending on whether acid neutralization is required, an added base, such as triethylamine ($Et_3N$), diisopropylethylamine ($(i-Pr)_2NEt$), or pyridine, may be used. Many additional methods for converting a carboxylic acid to an amide are known, and can be found in standard reference books, such as "Compendium of Organic Synthetic Methods", Vol. I–VI (published by Wiley-Interscience), or Bodansky, "The Practice of Peptide Synthesis" (published by Springer-Verlag). Compound I-2 is converted to the oxazole derivative I-4 through a standard two-step process. First, compound I-2 is cyclized under dehydrating conditions, preferably with the Burgess reagent (*Org. Synth. Coll. Vol. VI* 1988, 788) as described by Meyers (*J. Org. Chem.* 1996, 61, 8207), to afford the oxazoline derivative. I-3. Subsequent oxidization according to the general methodology developed by Barrish (*J. Org. Chem.* 1993, 58, 4494) affords the oxazole derivative I-4. Other methods for the preparation of oxazoles from oxazolines are known, several of which are described in a recent review by Meyers (*Tetrahedron* 1994, 50, 2297). The methyl ester of I-4 is cleaved to the corresponding carboxylic acid (I-5) using nucleophilic conditions, such as lithium iodide in refluxing pyridine. Other methods for the nucleophilic cleavage of methyl esters can be found in standard reference volumes, such as Greene, "Protective Groups in Organic Synthesis" (published by Wiley-Interscience). Nucleophilic conditions are preferable in this instance, as concomitant cleavage of the ethyl ester might be expected under standard saponification conditions. Compound I-5 is converted to an activated form of the acid using 1,1'-carbonyl diimidazole, and the activated form is reacted with an appropriate amine, for instance 2-[(3-amino-1-propyl)amino]pyridine dihydrochloride, to afford the amide derivative I-6. As discussed above, a variety of other methods might be used to convert acid I-5 to the amide I-6. The ethyl ester of I-6 is hydrolyzed using aqueous base, for example, LiOH in aqueous THF or NaOH in aqueous methanol or ethanol, and the intermediate carboxylate salt is acidified with a suitable acid, for instance TFA or HCl, to afford the carboxylic acid I-7. Alternatively, the intermediate carboxylate salt can be isolated, if desired, or a carboxylate salt of the free carboxylic acid can be prepared by methods well-known to those of skill in the art.

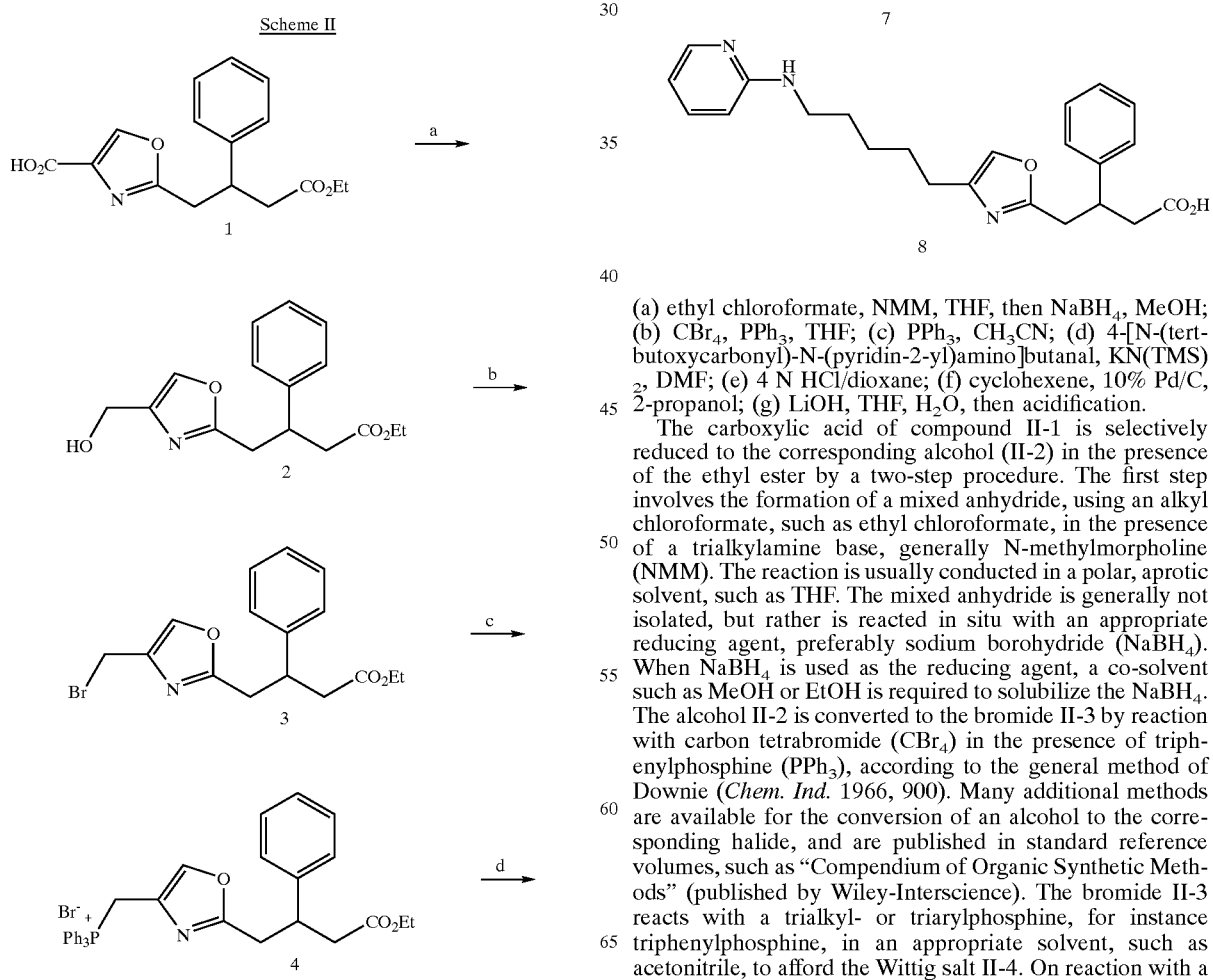

(a) ethyl chloroformate, NMM, THF, then NaBH$_4$, MeOH; (b) CBr$_4$, PPh$_3$, THF; (c) PPh$_3$, CH$_3$CN; (d) 4-[N-(tert-butoxycarbonyl)-N-(pyridin-2-yl)amino]butanal, KN(TMS)$_2$, DMF; (e) 4 N HCl/dioxane; (f) cyclohexene, 10% Pd/C, 2-propanol; (g) LiOH, THF, H$_2$O, then acidification.

The carboxylic acid of compound II-1 is selectively reduced to the corresponding alcohol (II-2) in the presence of the ethyl ester by a two-step procedure. The first step involves the formation of a mixed anhydride, using an alkyl chloroformate, such as ethyl chloroformate, in the presence of a trialkylamine base, generally N-methylmorpholine (NMM). The reaction is usually conducted in a polar, aprotic solvent, such as THF. The mixed anhydride is generally not isolated, but rather is reacted in situ with an appropriate reducing agent, preferably sodium borohydride (NaBH$_4$). When NaBH$_4$ is used as the reducing agent, a co-solvent such as MeOH or EtOH is required to solubilize the NaBH$_4$. The alcohol II-2 is converted to the bromide II-3 by reaction with carbon tetrabromide (CBr$_4$) in the presence of triphenylphosphine (PPh$_3$), according to the general method of Downie (*Chem. Ind.* 1966, 900). Many additional methods are available for the conversion of an alcohol to the corresponding halide, and are published in standard reference volumes, such as "Compendium of Organic Synthetic Methods" (published by Wiley-Interscience). The bromide II-3 reacts with a trialkyl- or triarylphosphine, for instance triphenylphosphine, in an appropriate solvent, such as acetonitrile, to afford the Wittig salt II-4. On reaction with a suitable base and a suitable aldehyde, for instance 4-[N-

(tert-butoxycarbonyl)-N-(pyridin-2-yl)amino]butanal, II-4 reacts in a well-known Witig reaction to afford olefin II-5. In the present instance, the conversion of II-4 to II-5 is accomplished optimally according to a general procedure described by Evans (*J. Am. Chem Soc.* 1992, 114, 9434). The tert-butoxycarbonyl protecting group in II-5 is removed under acidic conditions, such as 4 N HCl in 1,4-dioxane or TFA in $CH_2Cl_2$, to afford II-6. Conditions for removal of the tert-butoxycarbonyl protecting group are well-known to those of skill in the art, and several useful methods are described in standard reference volumes such as Greene "Protective Groups in Organic Synthesis". Both the olefin and N-oxide moieties of II-6 are reduced simultaneously using transfer hydrogenation conditions to afford II-7. Typically, this reaction is mediated by a palladium catalyst, preferably palladium metal on activated carbon, and occurs in an inert solvent, for instance methanol, ethanol, or 2-propanol. Cyclohexene, 1,4-cyclohexadiene, formic acid, and salts of formic acid, such as potassium formate or ammonium formate, are commonly used as the hydrogen transfer reagent in this type of reaction. The ethyl ester of II-7 is hydrolyzed as described in Scheme I to afford the carboxylic acid II-8.

Amide coupling reagents as used herein denote reagents which may be used to form peptide bonds. Typical coupling methods employ.carbodiimides, activated anhydrides and esters and acyl halides. Reagents such as EDC, DCC, DPPA, BOP reagent, HOBt, N-hydroxysuccinimide and oxalyl chloride are typical.

Coupling methods to form peptide bonds are generally well known to the art. The methods of peptide synthesis generally set forth by Bodansky et al., THE PRACTICE OF PEPTIDE SYNTHESIS, Springer-Verlag, Berlin, 1984, Ali et al. in *J. Med. Chem.*, 29, 984 (1986) and *J. Med. Chem.*, 30,2291 (1987) are generally illustrative of the technique and are incorporated herein by reference.

Typically, the amine or aniline is coupled via its free amino group to an appropriate carboxylic acid substrate using a suitable carbodiimide coupling agent, such as N,N' dicyclohexyl carbodiimide (DCC), optionally in the presence of catalysts such as 1-hydroxybenzotriazole (HOBt) and dimethylamino pyridine (DMAP). Other methods, such as the formation of activated esters, anhydrides or acid halides, of the free carboxyl of a suitably protected acid substrate, and subsequent reaction with the free amine of a suitably protected amine, optionally in the presence of a base, are also suitable. For example, a protected Boc-amino acid or Cbz-amidino benzoic acid is treated in an anhydrous solvent, such as methylene chloride or tetrahydrofuran (THF), in the presence of a base, such as N-methyl morpholine, DMAP or a trialkylamine, with isobutyl chloroformate to form the "activated anhydride", which is subsequently reacted with the free amine of a second protected amino acid or aniline.

Useful intermediates for preparing formula (I) compounds in which $R^2$ is a benzimidazole are disclosed in Nestor et al, *J. Med. Chem.* 1984, 27, 320. Representative methods for preparing benzimidazole compounds useful as intermediates in the present. invention are also common to the art and may be found, for instance, in EP-A 0 381 033.

Acid addition salts of the compounds are prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as $Li^+$, $Na^+$, $K^+$, $Ca^{++}$, $Mg^{++}$ and $NH_4+$ are specific examples of cations present in pharmaceutically acceptable salts.

This invention also provides a pharmaceutical composition which comprises a compound according to formula (I) and a pharmaceutically acceptable carrier. Accordingly, the compounds of formula (I) may be used in the manufacture of a medicament. Pharmaceutical compositions of the compounds of formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

The compounds described herein are antagonists of the vitronectin receptor, and are useful for treating diseases wherein the underlying pathology is attributable to ligand or cell which interacts with the vitronectin receptor. For instance, these compounds are useful for the treatment of diseases wherein loss of the bone matrix creates pathology. Thus, the instant compounds are useful for the treatment of ostoeporosis. hyperparathyroidism, Paget's disease, hypercalcemia of malignancy, osteolytic lesions produced by bone metastasis, bone loss due to immobilization or sex hormone deficiency. The compounds of this invention are also believed to have utility as antitumor, anti-angiogenic, anti-inflammatory and anti-metastatic agents, and be useful in the treatment of atherosclerosis and restenosis.

The compound is administered either orally or parenterally to the patient, in a manner such that the concentration of drug is sufficient to inhibit bone resorption, or other such indication. The pharmaceutical composition containing the compound is administered at an oral dose of between about 0.1 to about 50 mg/kg in a manner consistent with the condition of the patient. Preferably the oral dose would be about 0.5 to about 20 mg/kg. For acute therapy, parenteral administration is preferred. An intravenous infusion of the peptide in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg. The compounds are administered one to four times daily at a level to achieve a total daily dose of about 0.4 to about 400 mg/kg/day. The precise level and method by which the compounds are administered is readily determined by one routinely skilled in the art by comparing the blood level of the agent to the concentration required to have a therapeutic effect.

This invention further provides a method for treating osteoporosis or inhibiting bone loss which comprises administering stepwise or in physical combination a compound of formula (I) and other inhibitors of bone resorption, such as bisphosphonates (i.e., allendronate), hormone replacement therapy, anti-estrogens, or calcitonin. In addition, this invention provides a method of treatment using a compound of this invention and an anabolic agent, such as the bone morphogenic protein, iproflavone, useful in the prevention of bone loss and/or to increase bone mass.

Additionally, this invention provides a method of inhibiting tumor growth which comprises administering stepwise or in physical combination a compound of formula (I) and an antineoplastic agent. Compounds of the camptothecin analog class, such as topotecan, irinotecan and 9-aminocamptothecin, and platinum coordination complexes, such as cisplatin, ormaplatin and tetraplatin, are well known groups of antineoplastic agents. Compounds of the camptothecin analog class are described in U.S. Pat. Nos. 5,004,758, 4,604,463, 4,473,692, 4,545,880 4,342,776, 4,513,138, 4,399,276, EP Patent Application Publication Nos. 0 418 099 and 0 088 642, Wani, et al., *J. Med. Chem.*, 1986, 29, 2358, Wani, et al., *J. Med Chem.*, 1980, 23, 554, Wani, et al., *J. Med Chem.*, 1987, 30, 1774, and Nitta, et al., *Proc. 14th International Congr. Chemotherapy.*, 1985, *Anticancer Section* 1, 28, the entire disclosure of each which is hereby incorporated by reference. The platinum coordination complex, cisplatin, is available under the name Platinol® from Bristol Myers-Squibb Corporation. Useful formulations for cisplatin are described in U.S. Pat. Nos. 5,562,925 and 4,310,515, the entire disclosure of each which is hereby incorporated by reference.

In the method of inhibiting tumor growth which comprises administering stepwise or in physical combination a compound of formula (I) and an antineoplastic agent, the platinum coordination compound, for example cisplatin, can be administered using slow intravenous infusion. The preferred carrier is a dextrose/saline solution containing mannitol. The dose schedule of the platinum coordination compound may be on the basis of from about 1 to about 500 mg per square meter ($mg/m^2$) of body surface area per course of treatment. Infusions of the platinum coordiation compound may be given one to two times weekly, and the weekly treatments may be repeated several times. Using a compound of the camptothecin analog class in a parenteral administration, the course of therapy generally employed is from about 0.1 to about 300.0 $mg/m^2$ of body surface area per day for about five consecutive days. Most preferably, the course of therapy employed for topotecan is from about 1.0 to about 2.0 $mg/m^2$ of body surface area per day for about five consecutive days. Preferably, the course of therapy is repeated at least once at about a seven day to about a twenty-eight day interval.

The pharmaceutical composition may be formulated with both the compound of formula (I) and the antineoplastic agent in the same container, but formulation in different containers is preferred. When both agents are provided in solution form, they can be contained in an infusion/injection system for simultaneous administration or in a tandem arrangement.

For convenient administration of the compound of formula (I) and the antineoplastic agent at the same or different times, a kit is prepared, comprising, in a single container, such as a box, carton or other container, individual bottles, bags, vials or other containers each having an effective amount of the compound of formula (I) for parenteral administration, as described above, and an effective amount of the antineoplastic agent for parenteral administration, as described above. Such kit can comprise, for example, both pharmaceutical agents in separate containers or the same container, optionally as lyophilized plugs, and containers of solutions for reconstitution. A variation of this is to include the solution for reconstitution and the lyophilized plug in two chambers of a single container, which can be caused to admix prior to use. With such an arrangement, the antineoplastic agent and the compound of this invention may be packaged separately, as in two containers, or lyophilized together as a powder and provided in a single container.

When both agents are provided in solution form, they can be contained in an infusion/injection system for simultaneous administration or in a tandem arrangement. For example, the compound of formula (I) may be in an i.v. injectable form, or infusion bag linked in series, via tubing, to the antineoplastic agent in a second infusion bag. Using such a system, a patient can receive an initial bolus-type injection or infusion of the compound of formula (I) followed by an infusion of the antineoplastic agent.

The compounds may be tested in one of several biological assays to determine the concentration of compound which is required to have a given pharmacological effect.
Inhibition of Vitronectin Binding
Solid-Phase [$^3$H]-SK&F-107260 Binding to $\alpha_v\beta_3$ Human placenta or human platelet $\alpha_v\beta_3$ (0.1–0.3 mg/mL) in buffer T (containing 2 mM $CaCl_2$ and 1% octylglucoside) was diluted with buffer T containing 1 mM $CaCl_2$, 1 mM $MnCl_2$, 1 mM $MgCl_2$ (buffer A) and 0.05% $NaN_3$, and then immediately added to 96-well ELISA plates (Corning, New York, N.Y.) at 0.1 mL per well. 0.1–0.2 $\mu$g of $\alpha_v\beta_3$ was added per well. The plates were incubated overnight at 4° C. At the time of the experiment, the wells were washed once with buffer A and were incubated with 0.1 mL of 3.5% bovine serum albumin in the same buffer for 1 hr at room temperature. Following incubation the wells were aspirated completely and washed twice with 0.2 mL buffer A Compounds were dissolved in 100% DMSO to give a 2 mM stock solution, which was diluted with binding buffer (15 mM Tris-HCl (pH 7.4), 100 mM NaCl, 1 mM $CaCl_2$, 1 mM $MnCl_2$, 1 mM $MgCl_2$) to a final compound concentration of 100 $\mu$M. This solution is then diluted to the required final compound concentration. Various concentrations of unlabeled antagonists (0.001–100 $\mu$M) were added to the wells in triplicates, followed by the addition of 5.0 nM of [$^3$H]-SK&F-107260 (65–86 Ci/mmol).

The plates were incubated for 1 hr at room temperature. Following incubation the wells were aspirated completely and washed once with 0.2 mL of ice cold buffer A in a well-to-well fashion. The receptors were solubilized with 0.1 mL of 1% SDS and the bound [$^3$H]-SK&F-107260 was determined by liquid scintillation counting with the addition of 3 mL ReadySafe in a Beckman LS Liquid Scintillation Counter, with 40% efficiency. Nonspecific binding of [$^3$H]-SK&F-107260 was determined in the presence of 2 µM SK&F-107260 and was consistently less than 1% of total radioligand input. The $IC_{50}$ (concentration of the antagonist to inhibit 50% binding of [$^3$H]-SK&F-107260) was determined by a nonlinear, least squares curve-fitting routine, which was modified from the LUNDON-2 program. The $K_i$ (dissociation constant of the antagonist) was calculated according to the equation: $K_i=IC_{50}/(1+L/K_d)$, where L and $K_d$ were the concentration and the dissociation constant of [$^3$H]-SK&F-107260, respectively.

Compounds of the present invention inhibit vitronectin binding to SK&F 107260 in the concentration range of about 2.0–0.2 micomolar.

Compounds of this invention are also tested for in vitro and in vivo bone resorption in assays standard in the art for evaluating inhibition of bone formation, such as he pit formation assay disclosed in EP 528 587, which may also be performed using human osteoclasts in place of rat osteoclasts, and the ovarectomized rat model, described by Wronski et al., *Cells and Materials* 1991, Sup. 1, 69–74.

Vascular Smooth Muscle Cell Migration Assay

Rat or human aortic smooth muscle cells were used. The cell migration was monitored in a Transwell cell culture chamber by using a polycarbonate membrane with pores of 8 um (Costar). The lower surface of the filter was coated with vitronectin. Cells were suspended in DMEM supplemented with 0.2% bovine serum albumin at a concentration of $2.5–5.0 \times 10^6$ cells/mL, and were pretreated with test compound at various concentrations for 20 min at 20° C. The solvent alone was used as control. 0.2 mL of the cell suspension was placed in the upper compartment of the chamber. The lower compartment contained 0.6 mL of DMEM supplemented with 0.2% bovine serum albumin. Incubation was carried out at 37° C. in an atmosphere of 95% air/5% $CO_2$ for 24 hr. After incubation, the non-migrated cells on the upper surface of the filter were removed by gentle scraping. The filter was then fixed in methanol and stained with 10% Giemsa stain. Migration was measured either by a) counting the number of cells that had migrated to the lower surface of the filter or by b) extracting the stained cells with 10% acetic acid followed by determining the absorbance at 600 nM.

Thyroparathyroidectomized Rat Model

Each experimental group consists of 5–6 adult male Sprague-Dawley rats (250–400 g body weight). The rats are thyroparathyroidectomized (by the vendor, Taconic Farms) 7 days prior to use. All rats receive a replacement dose of thyroxine every 3 days. On receipt of the rats, circulating ionized calcium levels are measured in whole blood immediately after it has been withdrawn by tail venipuncture into heparinized tubes. Rats are included if the ionized Ca level (measured with a Ciba-Corning model 634 calcium pH analyzer) is <1.2 mM/L. Each rat is fitted with an indwelling venous and arterial catheter for the delivery of test material and for blood sampling respectively. The rats are then put on a diet of calcium-free chow and deionized water. Baseline Ca levels are measured and each rat is administered either control vehicle or human parathyroid hormone 1-34 peptide (hPTH1-34, dose 1.25 ug/kg/h in saline/0.1% bovine serum albumin, Bachem, Ca) or a mixture of hPTH1-34 and test material, by continuous intravenous infusion via the venous catheter using an external syringe pump. The calcemic response of each rat is measured at two-hourly intervals during the infusion period of 6–8 hours.

Human Osteoclast Resorption and Adhesion Assays

Pit resorption and adhesion assays have been developed and standardized using normal human osteoclasts derived from osteoclastoma tissue. Assay 1 was developed for the measurement of osteoclast pit volumes by laser confocal microscopy. Assay 2 was developed as a higher throughput screen in which collagen fragments (released during resorption) are measured by competitve ELISA.

Assay 1 (using laser confocal microscopy)

Aliquots of human osteoclastoma-derived cell suspensions are removed from liquid nitrogen strorage, warmed rapidly at 37° C. and washed ×1 in RPMI-1640 medium by centrifugation (1000 rpm, 5 mins at 4° C.).

The medium is aspirated and replaced with murine anti-HLA-DR antibody then diluted 1:3 in RPMI-1640 medium. The suspension is incubated for 30 mins on ice and mixed frequently.

The cells are washed ×2 with cold RPMI-1640 followed by centrifugation (1000 rpm, 5 mins at 4° C.) and the cells are then transferred to a sterile 15 ml centrifuge tube. The number of mononuclear cells are enumerated in an improved Neubauer counting chamber.

Sufficient magnetic beads (5/mononuclear cell), coated with goat anti-mouse IgG (Dynal, Great Neck, N.Y.) are removed from their stock bottle and placed into 5 ml of fresh medium (this washes away the toxic azide preservative). The medium is removed by immobilizing the beads on a magnet and is replaced with fresh medium.

The beads are mixed with the cells and the suspension is incubated for 30 mins on ice. The suspension is mixed frequently.

The bead-coated cells are immobilized on a magnet and the remaining cells (osteoclast-rich fraction) are decanted into a sterile 50 ml centrifuge tube.

Fresh medium is added to the bead-coated cells to dislodge any trapped osteoclasts. This wash process is repeated ×10. The bead-coated cells are discarded.

The viable osteoclasts are enumerated in a counting chamber, using fluorescein diacetate to label live cells. A large-bore disposable plastic pasteur pipet is used to add the sample to the chamber.

The osteoclasts are pelleted by centrifugation and the density adjusted to the appropriate number in EMEM medium (the number of osteoclasts is variable from tumor to tumor), supplemented with 10% fetal calf serum and 1.7 g/liter of sodium bicarbonate.

3 ml aliquots of the cell suspension (per compound treatment) are decanted into 15 ml centrifuge tubes. The cells are pelleted by centrifugation.

To each tube, 3 ml of the appropriate compound treatment are added (diluted to 50 uM in the EMEM medium). Also included are appropriate vehicle controls, a positive control (anti-vitronectin receptor murine monoclonal antibody [87MEM1] diluted to 100 ug/ml) and an isotype control ($IgG_{2a}$ diluted to 100 ug/ml). The samples are incubated at 37° C. for 30 mins.

0.5 ml aliquots of the cells are seeded onto sterile dentine slices in a 48-well plate and incubated at 37° C. for 2 hours. Each treatment is screened in quadruplicate.

The slices are washed in six changes of warm PBS (10 ml well in a 6-well plate) and then placed into fresh medium containing the compound treatment or control samples. The samples are incubated at 37° C. for 48 hours.

Tartrate Resistant Acid Phosphatase (TRAP) Procedure (Selective Stain for Cells of the Osteoclast Lineage)

The bone slices containing the attached osteoclasts are washed in phosphate buffered saline and fixed in 2% gluteraldehyde (in 0.2M sodium cacodylate) for 5 mins.

They are then washed in water and are incubated for 4 minutes in TRAP buffer at 37° C. (0.5 mg/ml naphthol AS-BI phosphate dissolved in N,N-dimethylformamide and mixed with 0.25 M citrate buffer (pH 4.5), containing 10 mM sodium tartrate.

Following a wash in cold water the slices are immersed in cold acetate buffer (0.1 M, pH 6.2) containing 1 mg/ml fast red garnet and incubated at 4° C. for 4 minutes.

Excess buffer is aspirated, and the slices are air dried following a wash in water.

The TRAP positive osteoclasts (brick red/ purple precipitate) are enumerated by bright-field microscopy and are then removed from the surface of the dentine by sonication.

Pit volumes are determined using the Nikon/Lasertec ILM21W confocal microscope.

Assay 2 (Using an ELISA Readout)

The human osteoclasts are enriched and prepared for compound screening as described in the initial 9 steps of Assay 1. For clarity, these steps are repeated hereinbelow.

Aliquots of human osteoclastoma-derived cell suspensions are removed from liquid nitrogen strorage, warmed rapidly at 37° C. and washed ×1 in RPMI-1640 medium by centrifugation (1000 rpm, 5 mins at 4° C.).

The medium is aspirated and replaced with murine anti-HLA-DR antibody then diluted 1:3 in RPMI-1640 medium. The suspension is incubated for 30 mins on ice and mixed frequently.

The cells are washed ×2 with cold RPMI-1640 followed by centrifugation (1000 rpm, 5 mins at 4° C.) and the cells are then transferred to a sterile 15 ml centrifuge tube. The number of mononuclear cells are enumerated in an improved Neubauer counting chamber.

Sufficient magnetic beads (5/mononuclear cell), coated with goat anti-mouse IgG (Dynal, Great Neck, N.Y.) are removed from their stock bottle and placed into 5 ml of fresh medium (this washes away the toxic azide preservative). The medium is removed by immobilizing the beads on a magnet and is replaced with fresh medium.

The beads are mixed with the cells and the suspension is incubated for 30 mins on ice. The suspension is mixed frequently.

The bead-coated cells are immobilized on a magnet and the remaining cells (osteoclast-rich fraction) are decanted into a sterile 50 ml centrifuge tube.

Fresh medium is added to the bead-coated cells to dislodge any trapped osteoclasts. This wash process is repeated ×10. The bead-coated cells are discarded.

The viable osteoclasts are enumerated in a counting chamber, using fluorescein diacetate to label live cells. A large-bore disposable plastic pasteur pipet is used to add the sample to the chamber.

The osteoclasts are pelleted by centrifugation and the density adjusted to the appropriate number in EMEM medium (the number of osteoclasts is variable from tumor to tumor), supplemented with 10% fetal calf serum and 1.7 g/liter of sodium bicarbonate.

In contrast to the method described above in Assay 1, the compounds are screened at 4 doses to obtain an $IC_{50}$, as outlined below:

The osteoclast preparations are preincubated for 30 minutes at 37° C. with test compound (4 doses) or controls.

They are then seeded onto bovine cortical bone slices in wells of a 48-well tissue culture plate and are incubated for a further 2 hours at 37° C.

The bone slices are washed in six changes of warm phosphate buffered saline (PBS), to remove non-adherent cells, and are then returned to wells of a 48 well plate containing fresh compound or controls.

The tissue culture plate is then incubated for 48 hours at 37° C.

The supernatants from each well are aspirated into individual tubes and are screened in a competitive ELISA that detects the c-telopeptide of type I collagen which is released during the resorption process. This is a commercially available ELISA (Osteometer, Denmark) that contains a rabbit antibody that specifically reacts with an 8-amino acid sequence (Glu-Lys-Ala-His-AspGly-Gly-Arg) that is present in the carboxy-terminal telopeptide of the a1-chain of type I collagen. The results are expressed as % inhibition of resorption compared to a vehicle control.

Human Osteoclast Adhesion Assay

The human osteoclasts are enriched and prepared for compound screening as described above in the inital 9 steps of Assay 1. For clarity, these steps are repeated hereinbelow.

Aliquots of human osteoclastoma-derived cell suspensions are removed from liquid nitrogen strorage, warmed rapidly at 37° C. and washed ×1 in RPMI-1640 medium by centrifugation (1000 rpm, 5 mins at 4° C.).

The medium is aspirated and replaced with murine anti-HLA-DR antibody then diluted 1:3 in RPMI-1640 medium. The suspension is incubated for 30 mins on ice and mixed frequently.

The cells are washed ×2 with cold RPMI-1640 followed by centrifugation (1000 rpm, 5 mins at 4° C.) and the cells are then transferred to a sterile 15 ml centrifuge tube. The number of mononuclear cells are enumerated in an improved Neubauer counting chamber.

Sufficient magnetic beads (5/mononuclear cell), coated with goat anti-mouse IgG (Dynal, Great Neck, N.Y.) are removed from their stock bottle and placed into 5 ml of fresh medium (this washes away the toxic azide preservative). The medium is removed by immobilizing the beads on a magnet and is replaced with fresh medium.

The beads are mixed with the cells and the suspension is incubated for 30 mins on ice. The suspension is mixed frequently.

The bead-coated cells are immobilized on a magnet and the remaining cells (osteoclast-rich fraction) are decanted into a sterile 50 ml centrifuge tube.

Fresh medium is added to the bead-coated cells to dislodge any trapped osteoclasts. This wash process is repeated ×10. The bead-coated cells are discarded.

The viable osteoclasts are enumerated in a counting chamber, using fluorescein diacetate to label live cells. A large-bore disposable plastic pasteur pipet is used to add the sample to the chamber.

The osteoclasts are pelleted by centrifugation and the density adjusted to the appropriate number in EMEM medium (the number of osteoclasts is variable from tumor to tumor), supplemented with 10% fetal calf serum and 1.7 g/liter of sodium bicarbonate.

Osteoclastoma-derived osteoclasts are preincubated with compound (4 doses) or controls at 37° C. for 30 minutes.

The cells are then seeded onto osteopontin-coated slides (human or rat osteopontin, 2.5 ug/ml) and incubated for 2 hours at 37° C.

Non adherent cells are removed by washing the slides vigorously in phosphate buffered saline and the cells remaining on the slides are fixed in acetone.

The osteoclasts are stained for tartrate-resistant acid phosphatase (TRAP), a selective marker for cells of this phenotype (see steps 15–17), and are enumerated by light microscopy. The results are expressed as % inhibition of adhesion compared to a vehicle control.

Cell Adhesion Assay
Cells and Cell Culture

Human embryonic kidney cells (HEK293 cells) were obtained from ATCC (Catalog No. CRL 1573). Cells were grown in Earl's minimal essential medium (EMEM) medium containing Earl's salts, 10% fetal bovine serum, 1% glutamine and 1% Penicillin-Steptomycin.

Constructs and Transfections

A 3.2 kb EcoRI-KpnI fragment of the $\alpha_v$ subunit and a 2.4 kb XbaI- XhoI fragment of the $\beta_3$ subunit were inserted into the EcoRI-EcoRV cloning sites of the pCDN vector (Aiyar et al., 1994 ) which contains a CMV promoter and a G418 selectable marker by blunt end ligation. For stable expression, 80×10$^6$ HEK 293 cells were electrotransformed with $\alpha_v+\beta_3$ constructs (20 μg DNA of each subunit) using a Gene Pulser (Hensley et al., 1994 ) and plated in 100 mm plates (5×10$^5$ cells/plate). After 48 hr, the growth medium was supplemented with 450 μg/mL Geneticin (G418 Sulfate, GIBCO-BRL, Bethesda, Md.). The cells were maintained in selection medium until the colonies were large enough to be assayed.

Immunocytochemical Analysis of Transfected Cells

To determine whether the HEK 293 transfectants expressed the vitronectin receptor, the cells were immobilized on glass microscope slides by centrifugation, fixed in acetone for 2 min at room temperature and air dried. Specific reactivity with 23C6, a monoclonal antibody specific for the $\alpha_v\beta_3$ complex was demonstrated using a standard indirect immunofluorescence method.

Cell Adhesion Studies

Corning 96-well ELISA plates were precoated overnight at 4° C. with 0.1 mL of human vitronectin (0.2 μg/mL in RPMI medium). At the time of the experiment, the plates were washed once with RPMI medium and blocked with 3.5% BSA in RPMI medium for 1 hr at room temperature. Transfected 293 cells were resuspended in RPMI medium, supplemented with 20 mM Hepes, pH 7.4 and 0.1% BSA at a density of 0.5×10$^6$ cells/mL. 0.1 mL of cell suspension was added to each well and incubated for 1 hr at 37° C., in the presence or absence of various $\alpha_v\beta_3$ antagonists. Following incubation, 0.025 mL of a 10% formaldehyde solution, pH 7.4, was added and the cells were fixed at room temperature for 10 min. The plates were washed 3 times with 0.2 mL of RPMI medium and the adherent cells were stained with 0.1 mL of 0.5% toluidine blue for 20 min at room temperature. Excess stain was removed by extensive washing with deionized water, The toluidine blue incorporated into cells was eluted by the addition of 0.1 mL of 50% ethanol containing 50 mM HCl. Cell adhesion was quantitated at an optical density of 600 nm on a microtiter plate reader (Titertek Multiskan MC, Sterling, Va.).

Solid-Phase $\alpha_v\beta_5$ Binding Assay

The vitronectin receptor $\alpha_v\beta_5$ was purified from human placenta. Receptor preparation was diluted with 50 mM Tris-HCl, pH 7.5, 100 mM NaCl, 1 mM CaCl$_2$, 1 mM MnCl$_2$, 1 mM MgCl$_2$ (buffer A) and was immediately added to 96-well ELISA plates at 0.1 ml per well. 0.1–0.2 μg of $\alpha_v\beta_3$ was added per well. The plates were incubated overnight at 4° C. At the time of the experiment, the wells were washed once with buffer A and were incubated with 0.1 ml of 3.5% bovine serum albumin in the same buffer for 1 hr at room temperature. Following incubation the wells were aspirated completely and washed twice with 0.2 ml buffer A.

In a [$^3$H]-SK&F-107260 competition assay, various concentrations of unlabeled antagonists (0.001–100 μM) were added to the wells, followed by the addition of 5.0 nM of [$^3$H]-SK&F-107260. The plates were incubated for 1 hr at room temperature. Following incubation the wells were aspirated completely and washed once with 0.2 ml of ice cold buffer A in a well-to-well fashion. The receptors were solubilized with 0.1 ml of 1% SDS and the bound [$^3$H]-SK&F-107260 was determined by liquid scintillation counting with the addition of 3 ml Ready Safe in a Beckman LS 6800 Liquid Scintillation Counter, with 40% efficiency. Nonspecific binding of [$^3$H]-SK&F-107260 was determined in the presence of 2 μM SK&F-107260 and was consistently less than 1% of total radioligand input. The IC$_{50}$ (concentration of the antagonist to inhibit 50% binding of [$^3$H]-SK&F-107260) was determined by a nonlinear, least squares curve-fitting routine, which was modified from the LUNDON-2 program. The K$_i$ (dissociation constant of the antagonist) was calculated according to Cheng and Prusoff equation: $K_i=IC_{50}/(1+L/K_d)$, where L and K$_d$ were the concentration and the dissociation constant of [$^3$H]-SK&F-107260, respectively.

Inhibition of RGD-mediated GPIIb-IIIa Binding
Purification of GPIIb-IIIa

Ten units of outdated, washed human platelets (obtained from Red Cross) were lyzed by gentle stirring in 3% octylglucoside, 20 mM Tris-HCl, pH 7.4, 140 mM NaCl, 2 mM CaCl$_2$ at 4° C. for 2 h. The lysate was centrifuged at 100,000 g for 1 h. The supernatant obtained was applied to a 5 mL lentil lectin sepharose 4B column (E.Y. Labs) preequilibrated with 20 mM Tris-HCl, pH 7.4, 100 mM NaCl, 2 mM CaCl$_2$, 1% octylglucoside (buffer A). After 2 h incubation, the column was washed with 50 mL cold buffer A. The lectin-retained GPIIb-IIIa was eluted with buffer A containing 10% dextrose. All procedures were performed at 4° C. The GPIIb-IIIa obtained was >95% pure as shown by SDS polyacrylamide gel electrophoresis.

Incorporation of GPIIb-IIIa in Liposomes

A mixture of phosphatidylserine (70%) and phosphatidylcholine (30%) (Avanti Polar Lipids) were dried to the walls of a glass tube under a stream of nitrogen. Purified GPIIb-IIIa was diluted to a final concentration of 0.5 mg/mL and mixed with the phospholipids in a protein:phospholipid ratio of 1:3 (w:w). The mixture was resuspended and sonicated in a bath sonicator for 5 min. The mixture was then dialyzed overnight using 12,000–14,000 molecular weight cutoff dialysis tubing against a 1000-fold excess of 50 mM Tris-HCl, pH 7.4, 100 mM NaCl, 2 mM CaCl2 (with 2 changes). The GPIIb-IIIa-containing liposomes wee centrifuged at 12,000 g for 15 min and resuspended in the dialysis buffer at a final protein concentration of approximately 1 mg/mL. The liposomes were stored at −70 C. until needed.

Competitive Binding to GPIIb-IIIa

The binding to the fibrinogen receptor (GPIIb-IIIa) was assayed by an indirect competitive binding method using [$^3$H]-SK&F-107260 as an RGD-type ligand. The binding assay was performed in a 96-well filtration plate assembly (Millipore Corporation, Bedford, Mass.) using 0.22 um hydrophilic durapore membranes. The wells were precoated with 0.2 mL of 10 μg/mL polylysine (Sigma Chemical Co., St. Louis, Mo.) at room temperature for 1 h to block nonspecific binding. Various concentrations of unlabeled benzazepines were added to the wells in quadruplicate. [$^3$H]-SK&F-107260 was applied to each well at a final concentration of 4.5 nM, followed by the addition of 1 μg of the purified platelet GPIIb-IIIa-containing liposomes. The mixtures were incubated for 1 h at room temperature. The GPIIb-IIIa-bound [3H]-SK&F-107260 was seperated from the unbound by filtration using a Millipore filtration manifold, followed by washing with ice-cold buffer (2 times, each 0.2 mL). Bound radioactivity remaining on the filters was counted in 1.5 mL Ready Solve (Beckman Instruments, Fullerton, Calif.) in a Beckman Liquid Scintillation Counter (Model LS6800), with 40% efficiency. Nonspecific binding was determined in the presence of 2 μM unlabeled SK&F-107260 and was consistently less than 0.14% of the total radioactivity added to the samples. All data points are the mean of quadruplicate. determinations.

Competition binding data were analyzed by a nonlinear least-squares curve fitting procedure. This method provides the IC50 of the antagonists (concentration of the antagonist which inhibits specific binding of [$^3$H]-SK&F-107260 by 50% at equilibrium). The IC50 is related to the equilibrium dissociation constant (Ki) of the antagonist based on the Cheng and Prusoff equation: Ki=IC50/(1+L/Kd), where L is the concentration of [3H]-SK&F-107260 used in the competitive binding assay (4.5 nM), and Kd is the dissociation constant of [3H]-SK&F-107260 which is 4.5 nM as determined by Scatchard analysis.

Preferred compounds of this invention have an affinity for the vitronectin receptor relative to the fibrinogen receptor of greater than 10:1. Most preferred compounds have a ratio of activity of greater than 100:1.

The efficacy of the compounds of formula (I) alone or in combination with an antineoplastic agent may be determined using several transplantable mouse tumor models. See U. S. Pat. Nos. 5,004,758 and 5,633,016 for details of these models The examples which follow are intended in no way to limit the scope of this invention, but are provided to illustrate how to make and use the compounds of this invention. Many other embodiments will be readily apparent to those skilled in the art.

General

Proton nuclear magnetic resonance ($^1$H NMR) spectra were recorded at 300 MHz, and chemical shifts are reported in parts per million (δ) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. CDCl$_3$ is deuteriochloroform, DMSO-d$_6$ is hexadeuteriodimethylsulfoxide, and CD$_3$OD is tetradeuteriomethanol. Mass spectra were obtained using electrospray (ES) ionization techniques. Elemental analyses were performed by Quantitative Technologies Inc., Whitehouse, N.J. Melting points were obtained on a Thomas-Hoover melting point apparatus and are uncorrected. All temperatures are reported in degrees Celsius. Analtech Silica Gel GF and E. Merck Silica Gel 60 F-254 thin layer plates were used for thin layer chromatography. Flash chromatography was carried out on E. Merck Kieselgel 60 (230–400 mesh) silica gel. Analytical and preparative HPLC were carried out on Beckman chromatographs. ODS refers to an octadecylsilyl-derivatized silica gel chromatographic support. YMC ODS-AQ® is an ODS chromatographic support and is a registered trademark of YMC Co. Ltd., Kyoto, Japan. PRP-1® is a polymeric (styrenedivinylbenzene) chromatographic support, and is a registered trademark of Hamilton Co., Reno, Nev. C-18 Mega Bond Elut® is a solid-phase extraction column that contains an octadecyl-bonded silica sorbent, and is a registered trademark of Varian Associates, Sunnyvale, Calif. Celite® is a filter aid composed of acid-washed diatomaceous silica, and is a registered trademark of Manville Corp., Denver, Colo.

Preparation 1

Preparation of 2-[(2-amino-1-ethyl)amino]2pyridine dihydrochloride a) 2-[[2-(tert-Butoxycarbonyl)amino-1-ethyl]amino]-1-oxopyridine A mixture of N-Boc-ethylenediamine (5.83 g, 36.39 mmole), 2-chloropyridine-N-oxide hydrochloride (7.25 g, g, 43.67 mmole), NaHCO$_3$ (15.29 g, 182 mmole), and tert-amyl alcohol (36 mL) was heated at reflux. After 47 hr, the dark brown mixture was cooled, diluted with CH$_2$Cl$_2$ (100 mL), and suction filtered. The filtrate was concentrated and the residue was reconcentrated from toluene. Silica gel chromatography (10% MeOH/CH$_2$Cl$_2$) gave the title compound (8.23 g, 89%) as a yellow solid: $^1$H NMR (250 MHz, CDCl$_3$) δ8.16 (dd, J=6.5, 1.3 Hz, 1 H), 7.05–7.30 (m, 2 H), 6.68 (br d, J=8.6 Hz 1 H), 6.50–6.65 (m, 1 H), 5.70–5.95 (m, 1 H), 3.25–3.60 (m, 4 H), 1.44 (s, 9 H); MS (ES) m/e 254 (M+H)$^+$.

b) 2-[[2-(tert-Butoxycarbonyl)amino-1-ethyl]amino]pyridine

A mixture of 2-[[2-(tert-butoxycarbonyl)amino-1-ethyl]amino]-1-oxopyridine (7.00 g, 27.64 mmole), 10% Pd/C (5.88 g, 5.53 mmole), cyclohexene (28 mL, 276.4 mmole), and isopropanol (110 mL) was heated at reflux. After 17 hr, the reaction was filtered through celite®, and the filtrate was concentrated. The yellow residue was reconcentrated from toluene, then was chromatographed on silica gel (5% MeOH/CHCl$_3$). The title compound (5.09 g, 78%) was obtained as a yellow oil: $^1$H NMR (400 MHz, CDCl$_3$) δ8.05–8.12 (m, 1 H), 7.37–7.46 (m, 1 H), 6.53–6.61 (m, 1 H), 6.41 (d, J=8.3 Hz, 1 H), 5.12 (br s, 1 H), 4.86 (br s, 1 H), 3.26–3.51 (m, 4 H), 1.44 (s, 9 H); MS (ES) m/e 238 (M+H)$^+$.

c) 2-[(2-Amino-1-ethyl)amino]pyridine dihydrochloride

4 N HCl/dioxane (54 mL) was added in a stream to a solution of 2-[[2-(tert-butoxycarbonyl)amino-1-ethyl]amino]pyridine (5.09 g, 21.45 mmole) in anhydrous CH$_2$Cl$_2$ (54 mL) at 0° C. under argon, then the mixture was warmed to RT. After 2 hr, the mixture was cooled to 0° C. and suction filtered. The solid was washed extensively with anhydrous Et$_2$O and dried in high vacuum at 40° C. to afford the title compound (4.27 g, 95%) as an off-white, somewhat hygroscopic solid: $^1$H NMR (400 MHz, CD$_3$OD) δ7.99–8.07 (m, 1 H), 7.92–7.98 (m, 1 H), 7.19 (d, J=9.1 Hz, 1 H), 6.98–7.04 (m, 1 H), 3.76 (t,J=6.2 Hz, 2 H). 3.27 (t, J=6.2 Hz, 2 H, partially obscured by residual solvent signal); MS (ES) m/e 138 (M+H)$^+$.

Preparation 2

Preparation of 2-[(3-amino-1-propyl)amino]pyridine dihydrochloride a) 2-[[3-(tert-Butoxycarbonyl)amino-1-propyl]amino]-1-oxopyridine According to the procedure of Preparation 1 (a), except substituting N-Boc-propylenediamine (3.33 g, 20 mmole) for the N-Boc-ethylenediamine, the title compound (4.90 g, 92%) was prepared: MS (ES) m/e 268 (M+H)$^+$.

b) 2-[[3-(tert-Butoxycarbonyl)amino-1-propyl]amino] pyridine

According to the procedure of Preparation 1 (b), except substituting 2-[[3-(tert-butoxycarbonyl)amino-1-propyl] amino]-1-oxopyridine (4.90 g, 18.3 mmole) for the 2-[[2-(tert-butoxycarbonyl)amino-1-ethyl]amino]-1-oxopyridine, the title compound (3.46 g, 75%) was prepared: MS (ES) m/e 252 (M+H)$^+$.

c) 2-[(3-Amino-1-propyl)amino]pyridine dihydrochloride

According to the procedure of Preparation 1 (c), except substituting 2-[[3-(tert-butoxycarbonyl)amino-1-propyl] amino]pyridine (3.46 g, 13.8 mmole) for the 2-[[2-(tert-butoxycarbonyl)amino-1-ethyl]amino]pyridine, the title compound (2.88 g, 93%) was prepared: MS (ES) m/e 152 (M+H)$^+$.

Preparation 3

Preparation of 2-[4-(4-amino-1-butyl)amino]pyridine a) 2-[[(tert-Butoxycarbonyl)amino-1-butyl]amino]-1-oxopyridine According to the procedure of Preparation 1 (a), except substituting N-Boc-butylenediamine (0.57 mL, 2.98 mmole) for the N-Boc-ethylenediamine, the title compound (0.42 g, 50%) was prepared: MS (ES) m/e 282 (M+H)$^+$.

b) 2-[[4-(tert-Butoxycarbonyl)amino-1-butyl]amino] pyridine

According to the procedure of Preparation 1 (b), except substituting 2-[[4(tert-butoxycarbonyl)amino-1-butyl] amino]-1-oxopyridine (0.88 g, 3.13 mmole) for the 2-[[2-(tert-butoxycarbonyl)amino-1-ethyl]amino]-1-oxopyridine, the crude title compound was prepared. This material was used without purification.

c) 2-[(4-Amino-1-butyl)amino]pyridine

Crude 2-[[4-(tert-butoxycarbonyl)amino-1-butyl]amino] pyridine (3.13 mmole) was treated with TFA (10 mL) in $CH_2Cl_2$ (10 mL). After 2 hr the mixture was concentrated under reduced pressure. The residue was taken up in 1.0 N NaOH (20 mL) and extracted with $CHCl_3$ (4×50 mL). The combined organic extracts were dried over $MgSO_4$, filtered, and concentrated under reduced pressure to give the title compound (122 mg, 24%) as a yellow oil: MS (ES) m/e 166 (M+H)$^+$.

Preparation 4

Preparation of 4-[N-(tert-butoxycarbonyl)-N-(pyridine-2-yl) amino]butanal.

a) 2-[(3-Hydroxy-1-butyl)amino]pyridine-N-oxide

A mixture of 4-amino-1-butanol (2.0 mL, 21.7 mmole), 2-chloropyridine-N-oxide hydrochloride (3.00 g, g, 18.0 mmole), $NaHCO_3$ (7.56 g, 90.0 mmole), and tert-amyl alcohol (22 mL) was heated at reflux. After 24 hr, the mixture was cooled and filtered, then the filtrate was concentrated under reduced pressure. Silica gel chromatography (10% $MeOH/CHCl_3$) gave the title compound (2.08 g, 63%) as a yellow solid: MS (ES) m/e 183 (M+H)$^+$.

b) 2-[N-(3-Hydroxy-1-butyl)-N-(tert-butoxycarbonyl) amino]pyridine-N-oxide

To a suspension of 2-[(3-hydroxy-1-butyl)amino] pyridine-N-oxide (895 mg, 4.91 mmole) in tert-butanol (5 mL) was added di-tert-butyl dicarbonate (1.18 g, 5.40 mmole). After 30 hr the mixture was concentrated under reduced pressure. The residue was chromatographed on silica gel (10% $MeOH/CHCl_3$) to give the title compound. (1.34 g, 97%) as a yellow solid: MS (ES) m/e 283 (M+H)$^+$.

c) 4-[N-(tert-Butoxycarbonyl)-N-(pyridin-2-yl)amino] butanal

To a solution of DMSO (0.31 mL, 3.54 mmole) in $CH_2Cl_2$ (5 mL) at −78° C. was added oxalyl chloride (0.13 mL, 1.77 mmole) dropwise. After 10 min, a solution of 2-[N-(3-hydroxy-1-butyl)-N-(tert-butoxycarbonyl)amino]pyridine-N-oxide (500 mg, 1.77 mmole) in $CH_2Cl_2$ (5 mL) was added dropwise. After 30 min, $Et_3N$ (0.81 mL, 5.84 mmole) was added, and the mixture was warmed gradually to RT. After 20 min, the mixture was diluted with $CH_2Cl_2$ (20 mL) and washed sequentially with 10 mL each $H_2O$, 10% HCl, $H_2O$, and brine. The organic layer was dried over $MgSO_4$, filtered, and concentrated under reduced pressure to give the title compound (455 mg, 92%) as a colorless oil. This was used without purification: MS. (ES) m/e 281 (M+H)$^+$.

Preparation 5

Preparation of ethyl (±)-4-(4-carboxy-1,3-oxazol-2-yl)-3-phenylbutanoate a) (±)-N-(4-Ethoxycarbonyl-3-phenylbutanoyl) serine methyl ester To a solution of ethyl (±) 4-carboxy-3-phenylbutanoate (1.00 g, 4.23 mmole) in dry DMF (20 mL) was added HOBt (686 mg, 5.08 mmole), $Et_3N$ (1.77 mL, 12.69 mmole), and EDC (974 mg, 5.08 mmole). After 30 min, L-serine methyl ester hydrochloride (790 mg, 5.08 mmole) was added. After 48 hr, the mixture was concentrated under reduced pressure. The residue was taken up in $CH_2Cl_2$ (50 mL) and washed sequentially with 20 mL each $H_2O$, saturated $NaHCO_3$, and $H_2O$. The organic layer was dried over $MgSO_4$, filtered, and concentrated under reduced pressure. The residue was chromatographed on silica gel (EtOAc) to give the title compound (961 mg, 67%) as a yellow oil: MS (ES) m/e 338 (M+H)$^+$.

b) Ethyl (±)-4-(4-methoxycarbonyl-1,3-oxazolin-2-yl)-3-phenylbutanoate

A solution of (±)-N-(4-ethoxycarbonyl-3-phenylbutanoyl) serine methyl ester (723 mg, 2.14 mmole) and Burgess reagent (613 mg, 2.57 mmole) in dry THF (10 mL) was heated at reflux under $N_2$. After 2 hr, the mixture was cooled to RT and concentrated under reduced pressure. The residue was chromatographed on silica gel (50% EtOAc/hexanes) to give the title compound (420 mg, 61%) as a colorless oil: MS (ES) m/e 320 (M+H)$^+$.

c) Ethyl (±)-4-(4-methoxycarbonyl-1,3-oxazol-2-yl)-3-phenylbutanoate

To a suspension of $CuBr_2$ (1.17 g, 5.26 mmole) in degassed (3×vacuum/$N_2$) $CH_2Cl_2$ (6 mL) was added hexamethylenetetramine (737 mg, 5.26 mmole) then DBU (0.78 mL, 5.26 mmole). After 5 min, a solution of ethyl (±)-4-(4-methoxycarbonyl-1,3-oxazolin-2-yl)-3-phenylbutanoate (420 mg, 1.32 mmole) in $CH_2Cl_2$ (2 mL) was added dropwise. After 6 hr, the mixture was filtered through a pad of silica gel (EtOAc) and the filtrate was concentrated under reduced pressure. The residue was chromatographed on silica gel (50% EtOAc/hexanes) to give the title compound (267 mg, 64%) as a white solid: MS (ES) m/e 318 (M+H)$^+$.

d) Ethyl (±)-4-(4-carboxy-1,3-oxazol-2-yl)-3-phenylbutanoate

A solution of ethyl (±)-4-(4-methoxycarbonyl-1,3-oxazol-2-yl)-3-phenylbutanoate (267 mg, 0.84 mmole) and LiI (338 mg, 2.52 mmole) in pyridine (5 mL) was heated to reflux. After 18 hr, the mixture was cooled to RT, poured into 10% HCl (150 mL), then extracted with $CH_2Cl_2$ (3×50 mL). The combined organic extracts were dried over $MgSO_4$, filtered, and concentrated to give the title compound (205 mg, 80%) as a white solid: MS (ES) m/e 304 (M+H)$^+$.

Preparation 6
Preparation of [2-(3-ethoxycarbonyl-2-phenylpropyl)-1,3-oxazol-4-yl]methyltriphenylphosphonium bromide a) Ethyl (±)-4-(4-hydroxymethyl-1,3-oxazol-2-yl)-3-phenylbutanoate To a solution of ethyl (±)-4-(4-carboxy-1,3-oxazol-2-yl)-3-phenylbutanoate (500 mg, 1.65 mmole) in dry THF (8 mL) was added 4-methylmorpholine (0.22 mL, 1.99 mmole) then ethyl chloroformate (0.19 mL, 1.99 mmole) at 0° C. After 10 min, NaBH$_4$ (249 mg, 6.59 mmole) was added all at once, then MeOH (8 mL) was added dropwise. After 30 min, the mixture was quenched with H$_2$O (20 mL) and extracted with EtOAc (3×20 mL). The combined organic extracts were dried over MgSO$_4$, filtered, and concentrated under reduced pressure. The residue was chromatographed on silica gel (80% EtOAc/hexanes) to give the title compound (371 mg, 78%) as a yellow oil: MS (ES) m/e 290 (M+H)$^+$.

b) Ethyl (±)-4-(4-bromomethyl-1,3-oxazol-2-yl)-3-phenylbutanoate

To a solution of ethyl (±)-4-(4-hydroxymethyl-1,3-oxazol-2-yl)-3-phenylbutanoate (1.3 g, 4.49 mmole) in dry THF (20 mL) was added PPh$_3$ (1.41 g, 5.39 mmole) then CBr$_4$ (1.79 g, 5.39 mmole) at 0° C. After 20 min, the mixture was warmed to RT. After 2 hr, the mixture was concentrated under reduced pressure. The residue was chromatographed on silica gel (20% EtOAc/hexanes) to give the title compound (1.38 g, 87%) as a colorless oil: MS (ES) m/e 352 (M+H)$^+$.

c) [2-(3-ethoxycarbonyl-2-phenylpropyl)-1,3-oxazol-4-yl]methyltriphenylphosphonium bromide A solution of ethyl (±)-4-(4-bromomethyl-1,3-oxazol-2-yl)-3-phenylbutanoate (1.0 g, 2.84 mmole) and PPh$_3$ (745 mg, 2.84 mmole) in dry CH$_3$CN (10 mL) was heated at reflux under N$_2$. After 3 hr, the mixture was cooled to RT and concentrated under reduced pressure. The residue was triturated with Et$_2$O (10 mL) to give the title compound (1.66 g, 95%) as a white powder: MS (ES) m/e 535 (M+H)$^+$.

Example 1
Preparation of (±)-3-phenyl-4-[4-[[[3-(pyridin-2-yl)amino-1-propyl]amino]carbonyl]-1,3-oxazol-2-yl]butanoic acid a) Ethyl (±)-3-phenyl-4-[4-[[[3-(pyridin-2-yl)amino-1-propyl]amino]carbonyl]-1,3-oxazol-2-yl]butanoate To a solution of ethyl (±)-4-(4-carboxy-1,3-oxazol-2-yl)-3-phenylbutanoate (100 mg, 0.33 mmole) in CH$_2$Cl$_2$ (2 mL) was added 1,1'-carbonyldiimidazole (80 mg, 0.49 mmole). After 2 hr, Et$_3$N (0.14 mL, 0.98 mmole) and 2-[(3-amino-1-propyl)amino]pyridine dihydrochloride (110 mg, 0.49 mmole) were added. After 4 h, the mixture was concentrated under reduced pressure. The residue was chromatographed on silica gel (75% EtOAc/hexanes) to give the title compound (131 mg, 91%) as a yellow oil: MS (ES) m/e 437 (M+H)$^+$.

b) (±)-3-Phenyl-4-[4-[[[3-(pyridin-2-yl)amino-1-propyl]amino]carbonyl]-1,3-oxazol-2-yl]butanoic acid To a solution of ethyl (±)-3-phenyl-4-[4-[[[3-(pyridin-2-yl)amino-1-propyl]amino]carbonyl]-1,3-oxazol-2-yl]butanoate (131 mg, 0.30 mmole) in 1:1 THF/H$_2$O (10 mL) was added 1N LiOH (0.36 mL, 0.36 mmole). After 18 hr, the mixture was concentrated under reduced pressure. The residue was dissolved in 20 mL H$_2$O then acidified to pH 6 using 10% HCl. The resulting cloudy solution was extracted with CH$_2$Cl$_2$ (3×75 mL). The organic extracts were dried over MgSO$_4$, filtered, and concentrated under reduced pressure. The residue was triturated with Et$_2$O to give the title compound as a white solid (63 mg, 51%) which was collected by filtration. MS (ES) m/e 409 (M+H)$^+$. Anal. Calcd for C$_{22}$H$_{24}$N$_4$O$_4$·0.75 H$_2$O, 1.5 HCl: C, 55.44; H, 5.71; N, 11.75. Found: C, 55.49; H, 5.54; N, 11.63.

Example 2
Preparation of (±)-3-phenyl-4-[4-[[[2-(pyridin-2-yl)amino-1-ethyl]amino]carbonyl]-1,3-oxazol-2-yl]butanoic acid a) Ethyl (±)-3-phenyl-4-[4-[[[2-(pyridin-2-yl)amino-1-ethyl]amino]carbonyl]-1,3-oxazol-2-yl]butanoate According to the procedure of Example 1 (a), except substituting 2-[(2-amino-1-ethyl)amino]pyridine dihydrochloride (129 mg, 0.74 mmole) for the 2-[(3-amino-1-propyl)amino]pyridine dihydrochloride, the title compound (157 mg, 76%) was prepared: MS (ES) m/e 423 (M+H)$^+$.

b) (±)-3-Phenyl-4-[4-[[[2-(pyridin-2-yl)amino-1-ethyl]amino]carbonyl]-1,3-oxazol-2-yl]butanoic acid To a solution of ethyl(±)-3-phenyl-4-[4-[[[2-(pyridin-2-yl)amino-1-ethyl]amino]carbonyl]-1,3-oxazol-2-yl]butanoate (157 mg, 0.37 mmole) in 1:1 THF/H$_2$O (4 mL) was added 1.0 N LiOH (0.56 mL, 0.56 mmole). After 24 hr, the mixture was washed with Et$_2$O (2×2 mL), and the pH of the aqueous layer was adjusted to 6 using 10% HCl. The solution was chromatographed on a C-18 Mega Bond Elut® column (50 mL H$_2$O then 50 mL 10% CH$_3$CN/H$_2$O). Fractions containing the product were pooled and lyophilized to give the title compound (48 mg, 33%) as a white powder: MS (ES) m/e 395 (M+H)$^+$. Anal. Calcd for C$_{21}$H$_{22}$N$_4$O$_4$· 0.75 HCl: C, 59.80; H, 5.44; N, 13.28. Found: C, 59.89; H, 5.50; N, 12.98.

Example 3
Preparation of (±)-3-phenyl-4-[4-[[[4-(pyridin-2-yl)amino-1-butyl]amino]carbonyl]-1,3-oxazol-2-yl]butanoic acid a) Ethyl (±)-3-phenyl-4-[4-[[[4-(pyridin-2-yl)amino-1-butyl]amino]carbonyl]-1,3-oxazol-2-yl]butanoate According to the procedure of Example 1 (a), except substituting 2-[(4amino-1-butyl)amino]pyridine (122 mg, 0.74 mmole) for the 2-[(3-amino-1-propyl)amino]pyridine dihydrochloride, the title compound (197 mg, 89%) was prepared: MS (ES) m/e 451 (M+H)$^+$.

b) (±)-3-Phenyl-4-[4-[[[4-(pyridin-2-yl)amino-1-butyl]amino]carbonyl]-1,3-oxazol-2-yl]butanoic acid To a solution of ethyl (±)-3-phenyl-4-[4-[[[4-(pyridin-2-yl)amino-1-butyl]amino]carbonyl]-1,3-oxazol-2-yl]butanoate (197 mg, 0.44 mmole) in 1:1 THF/H$_2$O (4 mL) was added 1.0 N LiOH (0.66 mL, 0.66 mmole). After 24 hr, the mixture was washed with Et$_2$O (2×2 mL), and the pH of the aqueous layer was adjusted to 6 using 10% HCl. The solution was chromatographed on a C-18 Mega Bond Elut® column (50 mL H$_2$O then 50 mL 20% CH$_3$CN/H$_2$O). Fractions containing the product were pooled and lyophilized to give the title compound (154 mg, 83%) as a white powder: MS (ES) m/e 423 (M+H)$^+$. Anal. Calcd for C$_{23}$H$_{26}$N$_4$O$_4$·0.75 H$_2$O: C, 63.36; H, 6.36; N, 12.85. Found: C, 63.55; H, 6.27; N, 12.50.

Example 4
Preparation of (±)-3-phenyl-4-[4-[5-(pyridin-2-yl)amino-1-pentyl]-1,3-oxazol-2-yl]butanoic acid a) Ethyl (±)-3-phenyl-4-[4-[5-[N-(1-oxopyridin-2-yl)-N-(tert-butoxycarbonyl)amino]-1-pentyl]-1,3-oxazol-2-yl]butanoate To a solution of 4-[N-(tert-butoxycarbonyl)-N-(pyridin-2-yl)amino]butanal (140 mg, 0.5 mmole) in dry DMF (5 mL) was added [2-(3-ethoxycarbonyl-2-phenylpropyl)-1,3-oxazol-4-yl]methyltriphenylphosphonium bromide (369 mg, 0.6 mmole) then KHMDS (1.2 mL, 0.6 mmole) dropwise at 0° C. After 3.5 hr, the mixture was diluted with H$_2$O (20 mL) and extracted with CH$_2$Cl$_2$ (3×20 mL). The combined organic extracts were dried over MgSO$_4$, filtered, and concentrated under reduced pressure. The residue was chromatographed on silica gel (3% MeOH in 1:1 EtOAc/CHCl$_3$)

to give the title compound (167 mg, 62%, mixture of E/Z isomers) as a yellow oil: MS (ES) m/e 536 (M+H)$^+$.

b) Ethyl(±)3-phenyl-4-[4-[5-(pyridin-2-yl)amino-1-pentyl]-1,3-oxazol-2-yl]butanoate Ethyl (±)-3-phenyl-4-[4-[5-[N-(1-oxopyridin-2-yl)-N-(tert-butoxycarbonyl)amino]-1-pentyl]-1,3-oxazol-2-yl]butanoate (167 mg, 0.31 mmole) was dissolved in 4 N HCl in dioxane (3 mL). After 1.5 hr, the mixture was concentrated under reduced pressure. The residue was dissolved in saturated NaHCO$_3$ (20 mL) and extracted with CH$_2$Cl$_2$ (2×20 mL). The combined organic extracts were dried over MgSO$_4$, filtered, and concentrated.

The above residue was combined with 10% Pd/C (33 mg) and cyclohexene (0.63 mL, 6.2 mmole) in isopropanol (5 mL), and the mixture was heated at reflux under N$_2$. After 18 hr, the mixture was cooled to RT and filtered through a pad of celite®, then the filtrate was concentrated under reduced pressure. The residue was chromatographed on silica gel (5% MeOH in 1:1 EtOAc/CHCl$_3$) to give the title compound (75 mg, 57% from a) as a white solid: MS (ES) m/e 422 (M+H)$^+$.

c) (±)-3-Phenyl-4-[4-[5-(pyridin-2-yl)amino-1-pentyl]-1,3-oxazol-2-yl]butanoic acid To a solution of ethyl (±)-3-phenyl-4-[4-[5-(pyridin-2-yl)amino-1-pentyl]-1,3-oxazol-2-yl]butanoate (75 mg, 0.18 mmole) in 1:1 THF/H$_2$O (2 mL) was added 1.0 N LiOH (0.27 mL, 0.27 mmole). After 18 hr, the pH was adjusted to 6 using 10% HCl; then the solution was concentrated under reduced pressure to remove the THF. The solution was chromatographed on a C-18 Mega Bond Elut® column (50 mL H$_2$O then 200 mL 20% CH$_3$CN/H$_2$O containing 0.1% TFA). Fractions containing the product were pooled and lyophilized to give the title compound (43 mg, 61%) as a yellow gum: MS (ES) m/e 394 (M+H)$^+$. Anal. Calcd for C$_{23}$H$_{27}$N$_3$O$_3$·0.098 CF$_3$CO$_2$H: C, 68.85; H, 6.75; N, 10.38. Found: C, 69.23; H, 7.00; N, 9.98.

Example 5
Parenteral Dosage Unit Composition

A preparation which contains 20 mg of the compound of Example 1 as a sterile dry powder is prepared as follows: 20 mg of the compound is dissolved in 15 mL of distilled water. The solution is filtered under sterile conditions into a 25 mL multi-dose ampoule and lyophilized. The powder is reconstituted by addition of 20 mL of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to-another mechanism for dispensing the drug, as in a bottle or bag for IV drip infusion or other injection-infusion system.

Example 6
Oral Dosage Unit Composition

A capsule for oral administration is prepared by mixing and milling 50 mg of the compound of Example 1 with 75 mg of lactose and 5 mg of magnesium stearate. The resulting powder is screened and filled into a hard gelatin capsule.

Example 7
Oral Dosage Unit Composition

A tablet for oral administration is prepared by mixing and granulating 20 mg of sucrose, 150 mg of calcium sulfate dihydrate and 50 mg of the compound of Example 1 with a 10% gelatin solution. The wet granules are screened, dried, mixed with 10 mg starch, 5 mg talc and 3 mg stearic acid; and compressed into a tablet.

The above description fully discloses how to make and use the present invention. However, the present invention. is not limited to the particular embodiments described hereinabove, but includes all modifications thereof within the scope of the following claims. The various references to journals, patents and other publications which are cited herein comprises the state of the art and are incorporated herein by reference as though fully set forth.

What is claimed is:

1. A compound according to formula (I):

$$R^2-Y-\underset{N}{\overset{O}{\diagdown}}\diagdown\underset{R^1}{\diagup}CO_2H \quad (I)$$

wherein:

Y is CR'R' or NR'C(O);

$R^1$ is —C$_{0-6}$alkyl-Ar, H, —C$_{1-6}$alkyl, —CN or —S(O)$_k$R$^g$;

$R^2$ is

[structure showing:
R'—N, R"—N with (O)$_u$ on ring N, (CR'$_2$)$_v$—W, ring with Q$^1$, Q$^2$, Q$^3$]  or

[structure showing:
(O)$_u$ on N, NR"—CR'$_2$—W, ring with Q$^1$, Q$^2$, Q$^3$, Q$^4$];

W is —(CHR$^g$)$_a$—U—(CHR$^g$)$_b$—;

U is absent or CO, CR$^g_2$, C(=CR$^g_2$), S(O)$_k$, O, NR$^g$, CR$^g$OR$^g$, CR$^g$(OR$^k$)CR$^g_2$, CR$^g_2$CR$^g$(OR$^k$), C(O)CR$^g_2$, CR$^g_2$C(O), CONR$^i$, NR$^i$CO, OC(O), C(O)O, C(S)O, OC(S), C(S)NR$^g$, NR$^g$C(S), S(O)$_2$NR$^g$, NR$^g$NR$^g$, NR$^g$CR$^g_2$, CR$^g_2$NR$^g$, CR$^g_2$O, OCR$^g_2$, C≡C, CR$^g$=CR$^g$, or Ar;

R$^g$ is H, C$_{1-6}$alkyl, C$_{3-7}$cycloalkyl-C$_{0-6}$alkyl or Ar—C$_{0-6}$alkyl;

R$^k$ is R$^g$, —C(O)R$^g$, or —C(O)OR$^f$;

R$^i$ is is H, C$_{1-6}$alkyl, C$_{3-7}$cycloalkyl-C$_{0-6}$alkyl, Ar—CO$_{0-6}$alkyl, or C$_{1-6}$alkyl substituted by one to three groups chosen from halogen, CN, NR$^g_2$, OR$^g$, SR$^g$, CO$_2$R$^g$, and CON(R$^g$)$_2$;

R$^f$ is H, C$_{1-6}$alkyl or Ar—CO$_{0-6}$alkyl;

R$^e$ is H, C$_{1-6}$alkyl, Ar—C$_{0-6}$alkyl, C$_{3-7}$cycloalkyl-C$_{0-6}$alkyl, or (CH$_2$)$_k$CO$_2$R$^g$;

R$^b$ and R$^c$ are independently selected from H, C$_{1-6}$alkyl, Ar—CO$_{0-6}$alkyl, Het-C$_{0-6}$alkyl, or C$_{3-6}$cycloalkyl-C$_{0-6}$alkyl, halogen, CF$_3$, OR$^f$, S(O)$_k$R$^f$, COR$^f$, NO$_2$, N(R$^f$)$_2$, CO(NR$^f$)$_2$, CH$_2$N(R$^f$)$_2$, or R$^b$ and R$^c$ are joined together to form a five or six membered aromatic or non-aromatic carbocyclic ring, optionally substituted by up to three substituents chosen from halogen, CF$_3$, C$_{1-4}$alkyl, OR$^f$, S(O)$_k$R$^f$, COR$^f$, CO$_2$R$^f$, OH, NO$_2$, N(R$^f$)$_2$, CO(NR$^f$)$_2$, and CH$_2$N(R$^f$)$_2$; or methylenedioxy;

Q$^1$, Q$^2$, Q$^3$ and Q$^4$ are independently C—R$^y$;

R' is H, C$_{1-6}$alkyl, Ar—C$_{0-6}$alkyl or C$_{3-6}$cycloalkyl-C$_{0-6}$alkyl;

R" is R', —C(O)R' or —C(O)OR';

$R^y$ is H, halo, —$OR^g$, —$SR^g$, —CN, —$NR^gR^k$, —$NO_2$, —$CF_3$, $CF_3S(O)_r$—, —$CO_2R^g$, —$COR^g$ or —$CONR^g_2$, or $C_{1-6}$alkyl optionally substituted by halo, —$OR^g$, —$SR^g$, —CN, —$NR^gR"$, —$NO_2$, —$CF_3$, R'S(O)$_r$—, —$CO_2R^g$, —$COR^g$ or —$CONR^g_2$;

a is 0, 1 or 2;
b is 0, 1 or 2;
k is 0, 1 or 2;
r is 0, 1 or 2;
s is 0, 1 or 2;
u is 0 or 1; and
v is 0 or 1;
or a pharmaceutically acceptable salt thereof.

2. A compound according to claim 1 in which $R^2$ is

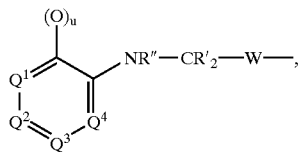

wherein $Q^1$, $Q^2$, and $Q^3$ are each $CR^y$, $Q^4$ is $CR^y$ and u is 0.

3. A compound according to claim 2 in which each R' is H, R" is H or $C_{1-6}$alkyl, W is —$(CH_2)_{1-4}$—, $Q^4$ is $CR^y$ and $R^y$ is H.

4. A compound according to claim 1 in which $R^2$ is

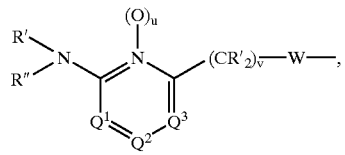

wherein $Q^1$, $Q^2$, and $Q^3$ are each CH and u is 0.

5. A compound according to claim 4 in which each R' is H, R" is H or $C_{1-6}$alkyl, v is 0 and W is —$(CH_2)_{1-4}$—.

6. A compound according to claim 1 in which $R^1$ is phenyl or benzyl.

7. A compound according to claim 6 which $R^1$ is phenyl.

8. A compound according to claim 1 in which Y is NHC(O).

9. A compound according to claim 1 which is:
(±)-3-phenyl-4-[4-[[[3-(pyridin-2-yl)amino-1-propyl]amino]carbonyl]-1,3-oxazol-2-yl]butanoic acid;
(±)-3-phenyl-4-[4-[[[2-(pyridin-2-yl)amino-1-ethyl]amino]carbonyl]-1,3-oxazol-2-yl]butanoic acid;
(±)-3-phenyl-4-[4-[[[4-(pyridin-2-yl)amino-1-butyl]amino]carbony]-1,3-oxazol-2-yl]butanoic acid; or
(±)-3-phenyl-4-[4-[5-(pyridin-2-yl)amino-1-pentyl]-1,3-oxazol-2-yl]butanoic acid;
or a pharmaceutically acceptable salt thereof.

10. A pharmaceutical composition which comprises a compound according to claim 1 and a pharmaceutically acceptable carrier.

11. A pharmaceutical composition which comprises a compound according to claim 1, an antineoplastic agent and a pharmaceutically acceptable carrier.

12. The pharmaceutical composition according to claim 11 wherein the antineoplastic agent is topotecan.

13. The pharmaceutical composition according to claim 11 wherein the antineoplastic agent is cisplatin.

14. A pharmaceutical composition which comprises a compound according to claim 1, an inhibitor of bone resorption and a pharmaceutically acceptable carrier.

15. A method of treating a disease state in which antagonism of the $\alpha_v\beta_3$ receptor is indicated which comprises administering to a subject in need thereof a compound according to claim 1.

16. A method of treating a-disease state in which antagonism of the $\alpha_v\beta_5$ receptor is indicated which comprises administering to a subject in need thereof a compound according to claim 1.

17. A method of treating osteoporosis which comprises administering to a subject in need thereof a compound according to claim 1.

18. A method for inhibiting angiogenesis which comprises administering to a subject in need thereof a compound according to claim 1.

19. A method for inhibiting tumor growth or tumor metastasis which comprises administering to a subject in need thereof a compound according to claim 1.

20. A method of treating-atherosclerosis or restenosis which comprises administering to a subject in need thereof a compound according to claim 1.

21. A method of treating inflammation which comprises administering to a subject in need thereof a compound according to claim 1.

22. A method of inhibiting tumor growth which comprises administering stepwise or in physical combination a compound according to claim 1 and an antineoplastic agent.

23. The method according to claim 22 wherein the antineoplastic agent is topotecan.

24. The method according to claim 22 wherein the antineoplastic agent is cisplatin.

25. A method of treating osteoporosis or inhibiting bone loss which comprises administering stepwise or in physical combination a compound according to claim 1 and an inhibitor of bone resorption.

26. A compound according to formula (II):

(II)

wherein:
Y is CR'R' or NR'C(O);
$R^1$ is —$C_{0-6}$alkyl-Ar, H, —$C_{1-6}$alkyl, —CN or —$S(O)_kR^g$;
$R^2$ is

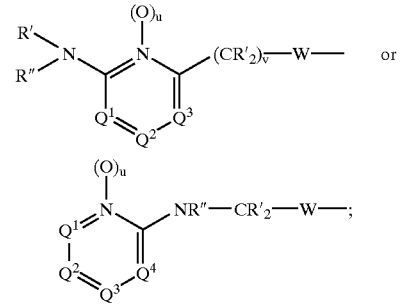

W is —$(CHR^g)_a$—U—$(CHR^g)_b$—;
U is absent or CO, $CR^g_2$, C(=$CR^g_2$), S(O)$_k$, O, $NR^g$, $CR^gOR^g$, $CR^g(OR^k)CR^g_2$, $CR^g_2CR^g(OR^k)$, C(O)$CR^g_2$, $CR^g_2C(O)$, $CONR^i$, $NR^iCO$, OC(O), C(O)O, C(S)O, OC(S), C(S)$NR^g$, $NR^gC(S)$, S(O)$_2NR^g$, $NR^gNR^g$, $NR^gCR^g_2$, $CR^g_2NR^g$, $CR^g_2O$, $OCR^g_2$, C≡C, $CR^g$=$CR^g$, or Ar;

$R^g$ is H, $C_{1-6}$alkyl, $C_{3-7}$cycloalkyl-$C_{0-6}$alkyl or Ar—$C_{0-6}$alkyl;

$R^k$ is $R^g$, —C(O)$R^g$, or —C(O)O$R^f$;

$R^i$ is is H, $C_{1-6}$alkyl, $C_{3-7}$cycloalkyl-$C_{0-6}$alkyl, Ar—$C_{0-6}$alkyl, or $C_{1-6}$alkyl substituted by one to three groups chosen from halogen, CN, N$R^g{}_2$, O$R^g$, S$R^g$, CO$_2R^g$, and CON($R^g$)$_2$;

$R^f$ is H, $C_{1-6}$alkyl or Ar—$C_{0-6}$alkyl;

$R^e$ is H, $C_{1-6}$alkyl, Ar—$C_{0-6}$alkyl, $C_{3-7}$cycloalkyl-$C_{0-6}$alkyl, or (CH$_2$)$_k$CO$_2R^g$;

$R^b$ and $R^c$ are independently selected from H, $C_{1-6}$alkyl, Ar—$C_{0-6}$alkyl, Het—$C_{0-6}$alkyl, or $C_{3-6}$cycloalkyl-$C_{0-6}$alkyl, halogen, CF$_3$, O$R^f$, S(O)$_k R^f$, CO$R^f$, NO$_2$, N($R^f$)$_2$, CO(N$R^f$)$_2$, CH$_2$N($R^f$)$_2$, or $R^b$ and $R^c$ are joined together to form a five or six membered aromatic or non-aromatic carbocyclic ring, optionally substituted by up to three substituents chosen from halogen, CF$_3$, $C_{1-4}$alkyl, O$R^f$, S(O)$_k R^f$, CO$R^f$, CO$_2R^f$, OH, NO$_2$, N($R^f$)$_2$, CO(N$R^f$)$_2$, and CH$_2$N($R^f$)$_2$; or methylenedioxy;

$Q^1$, $Q^2$, $Q^3$ and $Q^4$ are independently C—$R^y$;

R' is H, $C_{1-6}$alkyl, Ar—$C_{0-6}$alkyl or $C_{3-6}$cycloalkyl-$C_{0-6}$alkyl;

R" is R', —C(O)R' or —C(O)OR';

$R^y$ is H, halo, —O$R^g$, —S$R^g$, —CN, —N$R^g R^k$, —NO$_2$, —CF$_3$, CF$_3$S(O)$_r$—, —CO$_2R^g$, —CO$R^g$ or —CON$R^g{}_2$, or $C_{1-6}$alkyl optionally substituted by halo, —O$R^g$, —S$R^g$, —CN, —N$R^g$R", —NO$_2$, —CF$_3$, R'S(O)$_r$—, —CO$_2R^g$, —CO$R^g$ or —CON$R^g{}_2$;

a is 0, 1 or 2;

b is 0, 1 or 2;

k is 0, 1 or 2;

r is 0, 1 or 2;

s is 0, 1 or 2;

u is 0 or 1; and v is 0 or 1;

or a pharmaceutically acceptable salt thereof.

27. A process for preparing a compound of the formula (I) as defined in claim 1, which process comprises reacting a compound of formula (III) with a compound of formula (IV):

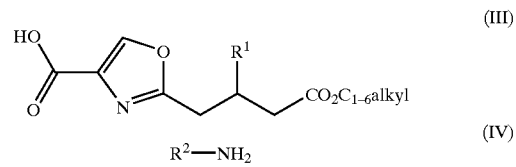

wherein $R^1$ and $R^2$ are as defined in formula (I), with any reactive functional groups protected;

and thereafter removing any protecting groups, and optionally forming a pharmaceutically acceptable salt.

* * * * *